United States Patent
Oepts et al.

(10) Patent No.: US 12,298,003 B2
(45) Date of Patent: May 13, 2025

(54) LIGHT SOURCE WITH DISINFECTION FUNCTION

(71) Applicant: SIGNIFY HOLDING B.V., Eindhoven (NL)

(72) Inventors: Wouter Oepts, Eindhoven (NL); Martinus Petrus Joseph Peeters, Weert (NL); René Theodorus Wegh, Veldhoven (NL)

(73) Assignee: SIGNIFY HOLDING B.V., Eindhoven (NL)

( * ) Notice: Subject to any disclaimer, the term of this patent is extended or adjusted under 35 U.S.C. 154(b) by 0 days.

(21) Appl. No.: 18/720,723

(22) PCT Filed: Dec. 6, 2022

(86) PCT No.: PCT/EP2022/084513
§ 371 (c)(1),
(2) Date: Jun. 17, 2024

(87) PCT Pub. No.: WO2023/110510
PCT Pub. Date: Jun. 22, 2023

(65) Prior Publication Data
US 2025/0052402 A1     Feb. 13, 2025

(30) Foreign Application Priority Data
Dec. 17, 2021  (EP) .................................... 21215538

(51) Int. Cl.
*F21V 9/38*     (2018.01)
*A61L 2/00*     (2006.01)
(Continued)

(52) U.S. Cl.
CPC ................ *F21V 9/38* (2018.02); *A61L 2/084* (2013.01); *A61L 2/10* (2013.01); *A61L 2/24* (2013.01);
(Continued)

(58) Field of Classification Search
CPC ..... F21V 9/30; F21V 9/32; F21V 9/35; F21V 9/38; F21V 9/45; A61L 2/0047;
(Continued)

(56) References Cited

U.S. PATENT DOCUMENTS

| 2016/0030610 A1 | 2/2016 | Peterson et al. |
| 2017/0030555 A1 | 2/2017 | Lalicki et al. |

(Continued)

*Primary Examiner* — Colin J Cattanach

(57) ABSTRACT

The invention provides a light generating system (1000) configured to generate system light (1001), wherein the light generating system (1000) comprises a first light generating device (110), wherein: (A) the first light generating device (110) comprises a first light source (10) and a first luminescent converter (210); (B) the first light source (10) comprises a solid state light source, wherein the first light source (10) is configured to generate first light source light (11) having a first light source centroid wavelength ($\lambda_s,1$) selected from the range of 380-420 inn; (C) the first luminescent converter (210) is configured to convert at least part of the first light source light (11) into first converter light (211) having a first converter centroid wavelength ($\lambda_c$, 1) selected from the green-yellow wavelength range; (D) the first light generating device (110) is configured to generate first device light (111) having a spectral power distribution in the wavelength range of 380-780 nm with at least 60% of the spectral power provided by the first light source light (11) and at maximum 40% of the spectral power provided by the first converter light (211).

15 Claims, 9 Drawing Sheets

(I)

(II)

(51) Int. Cl.
| | |
|---|---|
| *A61L 2/08* | (2006.01) |
| *A61L 2/10* | (2006.01) |
| *A61L 2/24* | (2006.01) |
| *A61L 2/26* | (2006.01) |
| *A61L 9/20* | (2006.01) |
| *A61L 12/06* | (2006.01) |
| *F21V 9/30* | (2018.01) |
| *F21V 9/32* | (2018.01) |
| *F21V 9/35* | (2018.01) |
| *F21V 9/45* | (2018.01) |
| *F21Y 113/00* | (2016.01) |
| *F21Y 113/10* | (2016.01) |
| *F21Y 113/13* | (2016.01) |
| *F21Y 113/20* | (2016.01) |
| *H01L 33/50* | (2010.01) |
| *H01L 33/52* | (2010.01) |
| *H01L 33/56* | (2010.01) |
| *H01L 33/58* | (2010.01) |
| *F21Y 113/17* | (2016.01) |

(52) U.S. Cl.
CPC ............... *A61L 2/26* (2013.01); *A61L 9/20* (2013.01); *A61L 2/0047* (2013.01); *A61L 12/063* (2013.01); *A61L 2202/11* (2013.01); *A61L 2202/14* (2013.01); *A61L 2209/11* (2013.01); *A61L 2209/12* (2013.01); *A61L 2209/15* (2013.01); *F21V 9/30* (2018.02); *F21V 9/32* (2018.02); *F21V 9/35* (2018.02); *F21V 9/45* (2018.02); *F21Y 2113/00* (2013.01); *F21Y 2113/10* (2016.08); *F21Y 2113/13* (2016.08); *F21Y 2113/17* (2016.08); *F21Y 2113/20* (2016.08); *F21Y 2113/30* (2023.05); *H01L 33/50* (2013.01); *H01L 33/501* (2013.01); *H01L 33/502* (2013.01); *H01L 33/504* (2013.01); *H01L 33/507* (2013.01); *H01L 33/508* (2013.01); *H01L 33/52* (2013.01); *H01L 33/56* (2013.01); *H01L 33/58* (2013.01)

(58) Field of Classification Search
CPC ........ A61L 2/084; A61L 2/10; A61L 2202/11; A61L 9/20; A61L 2209/12; A61L 12/063; F21Y 2113/10; F21Y 2113/30; F21Y 2113/00; F21Y 2113/13; F21Y 2113/17; F21Y 2113/20; H01L 33/50; H01L 33/501; H01L 33/502; H01L 33/504; H01L 33/507; H01L 33/508; H01L 33/52; H01L 33/56; H01L 33/58
See application file for complete search history.

(56) References Cited

U.S. PATENT DOCUMENTS

| | | |
|---|---|---|
| 2018/0147417 A1 | 5/2018 | Rantala |
| 2019/0247528 A1 | 8/2019 | Rodriguez |
| 2020/0390915 A1 | 12/2020 | David et al. |
| 2021/0030905 A1 | 2/2021 | Barron et al. |
| 2021/0187138 A1 | 6/2021 | Barron et al. |
| 2022/0290840 A1* | 9/2022 | Cornelissen .............. F21V 7/06 |

* cited by examiner

LIGHT SOURCE WITH DISINFECTION FUNCTION

CROSS-REFERENCE TO PRIOR APPLICATIONS

This application is the U.S. National Phase application under 35 U.S.C. § 371 of International Application No. PCT/EP2022/084513, filed on Dec. 6, 2022, which claims the benefit of European Patent Application No. 21215538.6, filed on Dec. 17, 2021. These applications are hereby incorporated by reference herein.

FIELD OF THE INVENTION

The invention relates to a light generating system and to a lighting device comprising such light generating system. Yet, the invention also relates to a method for treating at least part of a space or of an object.

BACKGROUND OF THE INVENTION

Light sources for emitting light with power in the range of 390-420 nm of the spectral power distribution are known in the art. US2020/0390915, for instance, describes a light source for emitting emitted light having a spectral power distribution (SPD) comprising: a plurality of light emitters including at least two violet solid-state emitters having different peak wavelengths; wherein said emitted light has a chromaticity which is within a Duv distance of less than 5E-3 from the Planckian locus, wherein the chromaticity is calculated using CIE 1964 100 CMFs; and wherein at least 25% of the power within the SPD is in the range 380-430 nm.

US 2020 390915 A1 discloses A light source for emitting emitted light having an SPD comprising: (a) a plurality of light emitters including at least one violet solid-state emitter; (b) at least one phosphor; wherein said light emitters and said at least one phosphor being configured such that: at least 25% of the power within the SPD is in the range 390-420 nm, and the emitted light has a chromaticity which is within a Duv distance of less than 5 points from the Planckian locus.

US 2016030610 A1 discloses a light fixture. The light fixture includes at least one first light source that emits at a peak wavelength in a range of approximately 380 nm to approximately 420 nm and at least one second light source that emits at a different peak wavelength, wherein a combined light output of the at least one first light source and the at least one second light source emits a colored light that is perceived as white light. The white light is defined by having a color rendering index (CRI) value of more than approximately 50. The at least one second light source that emits at a different peak wavelength consists of an xy coordinate on an International Commission on Illumination (CIE) 1931 xy color space diagram above a black body curve within a bounded area defined by a first line of approximately y=2.23989x-0.382773 and a second line of approximately y=1.1551x-0.195082. The combined light output has a proportion of spectral energy measured in the approximately 380 nm to approximately 420 nm range of greater than approximately 20%.

US 2017 030555 A1 discloses a device which inactivates microorganisms. The device includes a light emitter and at least one light-converting material arranged to convert at least a portion of light from the light emitter. Any light emitted from the light emitter and converted light emitted from the at least one light-converting material mixes to form a combined light, the combined light having a proportion of spectral energy measured in an approximately 380 nm to approximately 420 nm range of greater than approximately 20 percent. In another embodiment, the device includes a light emitter configured to emit light with wavelengths in a range of 380 to 420 nm, and at least one light-converting material including at least one optical brightener and configured to emit a second light. The first light exiting the device and the second light exiting the device mix to form a combined light, the combined light being white.

SUMMARY OF THE INVENTION

UV light has been used for disinfection for over 100 years. Wavelengths between about 190 nm and 300 nm may be strongly absorbed by nucleic acids, which may result in defects in an organism's genome. This may be desired for inactivating (killing), bacteria and viruses, but may also have undesired side effects for humans. Therefore, the selection of wavelength of radiation, intensity of radiation and duration of irradiation may be limited in environments where people may reside such as offices, public transport, cinema's, restaurants, shops, etc., thus limiting the disinfection capacity. Especially in such environments, additional measures of disinfection may be advantageous to prevent the spread of bacteria and viruses such as influenza or novel (corona) viruses like COVID-19, SARS, and MERS.

It appears desirable to produce systems, that provide alternative ways for air treatment, such as disinfection. Further, existing systems for disinfection may not easily be implemented in existing infrastructure, such as in existing buildings like offices, hospitality areas, etc. and/or may not easily be able to serve larger spaces. This may again increase the risk of contamination. Further, incorporation in HVAC systems may not lead to desirable effects and appears to be relatively complex. Further, existing systems may not be efficient, or may be relatively bulky, and may also not easily be incorporated in functional devices, such as e.g. luminaires.

Other disinfection systems may use one or more anti-microbial and/or anti-viral means to disinfect a space or an object. Examples of such means may be chemical agents which may raise concerns. For instance, the chemical agents may also be harmful for people and pets.

In embodiments, the disinfecting light, may especially comprise ultraviolet (UV) radiation (and/or optionally violet radiation), i.e., the light may comprise a wavelength selected from the ultraviolet wavelength range (and/or optionally the violet wavelength range). However, other wavelengths are herein not excluded. The ultraviolet wavelength range is defined as light in a wavelength range from 100 to 380 nm and can be divided into different types of UV light/UV wavelength ranges (Table 1). Different UV wavelengths of radiation may have different properties and thus may have different compatibility with human presence and may have different effects when used for disinfection (Table 1).

TABLE 1

Properties of different types of UV, violet, and NIR wavelength light

| Name | Short name | Wavelength (nm) | (Relative) sterilization effectiveness Bacteria | (Relative) sterilization effectiveness Viruses | Safe Radiation | Vitamin D generation | Ozone generation |
|---|---|---|---|---|---|---|---|
| Violet | V | 380-420 | +/− | +/− | + | | |
| Ultra-violet A | UV-A | 315-380 | + | − | + | | |
| Ultra-violet B | UV-B | 280-315 | + | +/− | +/− | + | |
| Near ultraviolet C | Near UV-C | 230-280 | ++ | ++ | − | | |
| Far ultra-violet C | Far UV-C | 190-230 | +++ | +++ | + | | +/− |
| Extreme ultraviolet C | Extreme UV-C | 100-190 | +++ | +++ | − | | + |

Each UV type/wavelength range may have different benefits and/or drawbacks. Relevant aspects may be (relative) sterilization effectiveness, safety (regarding radiation), and ozone production (as result of its radiation). Depending on an application a specific type of UV light or a specific combination of UV light types may be selected and provides superior performance over other types of UV light. UV-A may be (relatively) safe and may inactivate (kill) bacteria, but may be less effective in inactivating (killing) viruses. UV-B may be (relatively) safe when a low dose (i.e. low exposure time and/or low intensity) is used, may inactivate (kill) bacteria, and may be moderately effective in inactivating (killing) viruses. UV-B may also have the additional benefit that it can be used effectively in the production of vitamin D in a skin of a person or animal. Near UV-C may be relatively unsafe, but may effectively inactivating, especially kill bacteria and viruses. Far UV-C may also be effective in inactivating (killing) bacteria and viruses, but may be (relatively to other UV-C wavelength ranges) (rather) safe. Far-UV light may generate some ozone which may be harmful for human beings and animals. Extreme UV-C may also be effective in inactivating (killing) bacteria and viruses, but may be relatively unsafe. Extreme UV-C may generate ozone which may be undesired when exposed to human beings or animals. In some application ozone may be desired and may contribute to disinfection, but then its shielding from humans and animals may be desired. Hence, in the table "+" for ozone production especially implies that ozone is produced which may be useful for disinfection applications, but may be harmful for humans/animals when they are exposed to it. Hence, in many applications this "+" may actually be undesired while in others, it may be desired. The types of light indicated in above table may in embodiments be used to sanitize air and/or surfaces.

The terms "inactivating" and "killing" with respect to a virus may herein especially refer to damaging the virus in such a way that the virus can no longer infect and/or reproduce in a host cell, i.e., the virus may be (essentially) harmless after inactivation or killing.

As indicated by M. McLean et al., in Journal of Hospital Infection, Volume 88, Issue 1, September 2014, Pages 1-11, https://doi.org/10.1016/j.jhin.2014.06.004, which is herein incorporated by reference, violet-blue light, particularly 405 nm light, has significant antimicrobial properties against a wide range of bacterial and fungal pathogens. Further, R. Rathnasinghe et al., in Scientific Reports https://doi: 10.1038/s41598-021-97797-0, and/or doi: https://doi.org/10.1101/2021.03.14.435337 seems to demonstrate increased susceptibility of lipid-enveloped respiratory pathogens of importance such as SARS-CoV-2 (causative agent of COVID-19) as well as the influenza A virus to 405 nm, visible light in the absence of exogenous photosensitizers indicating a potential porphyrin-independent alternative mechanism of visible light mediated viral inactivation.

The application of such light may not be straightforward, as it may undesirably change the spectral properties of the light, and may not be attractive for people or have other undesirable effects, e.g. unpleasant environment to work or relax.

Hence, it is an aspect of the invention to provide an alternative light generating system, which preferably further at least partly obviates one or more of above-described drawbacks. The present invention may have as object to overcome or ameliorate at least one of the disadvantages of the prior art, or to provide a useful alternative.

According to a first aspect, the invention provides a light generating system configured to generate system light. Especially, the light generating system comprises a first light generating device. In embodiments, the first light generating device may comprise a first light source and a first luminescent converter. Especially, the first light source may comprise a solid state light source. In specific embodiments, the first light source may be configured to generate first light source light having a first light source centroid wavelength ($\lambda_{s,1}$), especially selected from the range of 380-430 nm, more especially 380-420 nm. Further, in embodiments the first luminescent converter may be configured to convert at least part of the first light source light into first converter light. The first converter light may especially have a first converter centroid wavelength ($\lambda_{c,1}$) selected from the green-yellow wavelength range. Especially, the first light generating device may be configured to generate first device light comprising the first light source light and the first converter light. Especially, the first light generating device may be configured to generate first device light having a spectral power distribution in the wavelength range of 380-780 nm with at least 60% of the spectral power provided by the first light source light and at maximum 40% of the spectral power provided by the first converter light. Therefore, especially the invention provides in embodiments a light generating system configured to generate system light, wherein the light generating system comprises a first light generating device, wherein: (A) the first light generating device comprises a first light source and a first luminescent converter; (B) the first light source comprises a solid state light source, wherein the first light source is configured to generate first light source light having a first light source centroid wavelength ($\lambda_{s,1}$) selected from the range of 380-430 nm, more especially 380-420 nm; (C) the first luminescent converter is configured to convert at least part of the first light source light into first converter light having a first converter centroid wavelength ($\lambda_{c,1}$) selected from the green-yellow wavelength range; and (E) the first light generating device is configured to generate first device light comprising the first light source light and the first converter light, more especially configured to generate first device light having a spectral power distribution in the wavelength range of 380-780 nm with at least 60% of the spectral power provided by the first light source light and at maximum 40% of the spectral power provided by the first converter light. In specific embodiments, the first light generating device may be combined with a second light generating device, different from the first light generating device, and configured to generate (in an operational mode) white system light (see also below).

With such system, it is possible to provide light, such as white or whitish, (system) light having the effect that viral and/or bacterial load may be reduced due to the short wavelength radiation of the first light generating device. Further, it appears that the efficiency and/or efficacy is increased due to the presence of the luminescent material of the first light generating device. With such system, it may also be possible to provide light for specific purposes, like general lighting, accent lighting, wall washing, etc. etc., while at the same time, or optionally alternatingly, light may be provided which may reduce viral and/or bacterial load. Further, in embodiments due to the (white-type) light that is added via the first light generating device to the white light of a second light generating device (see also below), it is possible to provide white (system) light with an additional effect, i.e. reduce viral and/or bacterial load may be reduced. Further, with the present system functional light may be provided that has a higher efficiency than purely providing the short wavelength radiation. Hence, the present invention may also provide a system able to provide white light with a color point close to the black body locus and having substantial viral and/or bacterial load reduction.

As indicated above, the light generating system may especially be configured to generate system light. In embodiments, in an operational mode, the system light may comprise the first device light. In other operational modes, if any, the system light may comprise also other light, should the system comprise one or more other type of light generating devices (see also embodiments below).

The first light generating device may comprise one or more first light sources. The one or more light sources may be configured to generate first light source light.

The term "light source" may in principle relate to any light source known in the art. It may be a conventional (tungsten) light bulb, a low pressure mercury lamp, a high pressure mercury lamp, a fluorescent lamp, a LED (light emissive diode). In a specific embodiment, the light source comprises a solid state LED light source (such as a LED or laser diode (or "diode laser")). The term "light source" may also relate to a plurality of light sources, such as 2-200 (solid state) LED light sources. Hence, the term LED may also refer to a plurality of LEDs. Further, the term "light source" may in embodiments also refer to a so-called chips-on-board (COB) light source. The term "COB" especially refers to LED chips in the form of a semiconductor chip that is neither encased nor connected but directly mounted onto a substrate, such as a PCB. Hence, a plurality of light emitting semiconductor light sources may be configured on the same substrate. In embodiments, a COB is a multi LED chip configured together as a single lighting module.

The light source may have a light escape surface. Referring to conventional light sources such as light bulbs or fluorescent lamps, it may be outer surface of the glass or quartz envelope. For LED's it may for instance be the LED die, or when a resin is applied to the LED die, the outer surface of the resin. In principle, it may also be the terminal end of a fiber. The term escape surface especially relates to that part of the light source, where the light actually leaves or escapes from the light source. The light source is configured to provide a beam of light. This beam of light (thus) escapes from the light exit surface of the light source.

Likewise, a light generating device may comprise a light escape surface, such as an end window. Further, likewise a light generating system may comprise a light escape surface, such as an end window.

The term "light source" may refer to a semiconductor light-emitting device, such as a light emitting diode (LEDs), a resonant cavity light emitting diode (RCLED), a vertical cavity laser diode (VCSELs), an edge emitting laser, etc . . . The term "light source" may also refer to an organic light-emitting diode (OLED), such as a passive-matrix (PMOLED) or an active-matrix (AMOLED). In a specific embodiment, the light source comprises a solid-state light source (such as a LED or laser diode). In an embodiment, the light source comprises a LED (light emitting diode). The terms "light source" or "solid state light source" may also refer to a superluminescent diode (SLED). The term LED may also refer to a plurality of LEDs.

The term "light source" may also relate to a plurality of (essentially identical (or different)) light sources, such as 2-2000 solid state light sources. In embodiments, the light source may comprise one or more micro-optical elements (array of micro lenses) downstream of a single solid-state light source, such as a LED, or downstream of a plurality of solid-state light sources (i.e. e.g. shared by multiple LEDs). In embodiments, the light source may comprise a LED with on-chip optics. In embodiments, the light source comprises a pixelated single LED (with or without optics) (offering in embodiments on-chip beam steering).

In embodiments, the light source may be configured to provide primary radiation, which is used as such, such as e.g. a blue light source, like a blue LED, or a green light source, such as a green LED, and a red light source, such as a red LED. Such LEDs, which may not comprise a luminescent material ("phosphor") may be indicated as direct color LEDs.

In other embodiments, however, the light source may be configured to provide primary radiation and part of the primary radiation is converted into secondary radiation. Secondary radiation may be based on conversion by a luminescent material. The secondary radiation may therefore also be indicated as luminescent material radiation. The luminescent material may in embodiments be comprised by the light source, such as a LED with a luminescent material layer or dome comprising luminescent material. Such LEDs may be indicated as phosphor converted LEDs or PC LEDs (phosphor converted LEDs). In other embodiments, the luminescent material may be configured at some distance ("remote") from the light source, such as a LED with a luminescent material layer not in physical contact with a die of the LED. Hence, in specific embodiments the light source may be a light source that during operation emits at least light at wavelength selected from the range of 380-470 nm. However, other wavelengths may also be possible. This light may partially be used by the luminescent material.

In embodiments, the light generating device may comprise a luminescent material. In embodiments, the light generating device may comprise a PC LED. In other embodiments, the light generating device may comprise a direct LED (i.e. no phosphor). In embodiments, the light generating device may comprise a laser device, like a laser diode. In embodiments, the light generating device may comprise a superluminescent diode. Hence, in specific embodiments, the light source may be selected from the group of laser diodes and superluminescent diodes. In other embodiments, the light source may comprise an LED.

The light source may especially be configured to generate light source light having an optical axis (O), (a beam shape,) and a spectral power distribution. The light source light may in embodiments comprise one or more bands, having band widths as known for lasers.

The term "light source" may (thus) refer to a light generating element as such, like e.g. a solid state light source, or e.g. to a package of the light generating element, such as a solid state light source, and one or more of a luminescent material comprising element and (other) optics, like a lens, a collimator. A light converter element ("converter element" or "converter") may comprise a luminescent material comprising element. For instance, a solid state light source as such, like a blue LED, is a light source. A combination of a solid state light source (as light generating element) and a light converter element, such as a blue LED and a light converter element, optically coupled to the solid state light source, may also be a light source (but may also be indicated as light generating device). Hence, a white LED is a light source (but may e.g. also be indicated as (white) light generating device).

The term "light source" herein may also refer to a light source comprising a solid state light source, such as an LED or a laser diode or a superluminescent diode.

The "term light source" may (thus) in embodiments also refer to a light source that is (also) based on conversion of light, such as a light source in combination with a luminescent converter material. Hence, the term "light source" may also refer to a combination of a LED with a luminescent material configured to convert at least part of the LED radiation, or to a combination of a (diode) laser with a luminescent material configured to convert at least part of the (diode) laser radiation.

In embodiments, the term "light source" may also refer to a combination of a light source, like a LED, and an optical filter, which may change the spectral power distribution of the light generated by the light source. Especially, the "term light generating device" may be used to address a light source and further (optical components), like an optical filter and/or a beam shaping element, etc.

The phrases "different light sources" or "a plurality of different light sources", and similar phrases, may in embodiments refer to a plurality of solid-state light sources selected from at least two different bins. Likewise, the phrases "identical light sources" or "a plurality of same light sources", and similar phrases, may in embodiments refer to a plurality of solid-state light sources selected from the same bin.

The term "solid state light source", or "solid state material light source", and similar terms, may especially refer to semiconductor light sources, such as a light emitting diode (LED), a diode laser, or a superluminescent diode.

Especially, the term "light generating device" may refer to a device comprising a solid state light source, like a light emitting diode (LED).

As indicated above, the light generating system may comprise a first light generating device. The term "first light generating device" may also refer to a plurality of first light generating devices, of which two or more may be same and/or of which two or more may be different. Especially, the first light generating device may comprise a first light source and a first luminescent converter.

In embodiments, the first light source may comprise a solid state light source. Further, as indicated above, the term "first light source" may also refer to a plurality of first light sources, of which two or more may be same and/or of which two or more may be different. Especially, the first light source may comprise a solid state light source, like a laser diode or a LED, especially a LED. Especially, when there are more than one first light sources, the first light sources may be of the same bin.

In embodiments, the first light source may be configured to generate first light source light having a wavelength selected from the 380-430 nm, more especially 380-420 nm wavelength range, more especially from the range of 395-415 nm, yet even more especially selected from the range of 400-410 nm. More especially, the first light source may be configured to generate first light source light having a peak wavelength selected from the 380-430 nm wavelength range, more especially from the range of 380-420 nm, such as in embodiments 395-415 nm, yet even more especially selected from the range of 400-410 nm.

Yet, in embodiments, the first light source may be configured to generate first light source light having a first light source centroid wavelength ($\lambda_{s,1}$) selected from the range of 380-430 nm, more especially 380-420 nm. With such light, it may be possible to reduce the viral load and/or bacterial load. More especially, the first light source centroid wavelength ($\lambda_{s,1}$) may be selected from the range of 395-415 nm. Especially, wavelengths around about 405 nm may be suitable. Hence, in further specific embodiments the first light source centroid wavelength ($\lambda_{s,1}$) may be selected from the range of 400-410 nm.

The term "centroid wavelength", also indicated as kc, is known in the art, and refers to the wavelength value where half of the light energy is at shorter and half the energy is at longer wavelengths; the value is stated in nanometers (nm). It is the wavelength that divides the integral of a spectral power distribution into two equal parts as expressed by the formula $\lambda_c = \varepsilon \lambda^* I(\lambda)/(\varepsilon\ I(\lambda))$, where the summation is over the wavelength range of interest, and $I(\lambda)$ is the spectral energy density (i.e. the integration of the product of the wavelength and the intensity over the emission band normalized to the integrated intensity). The centroid wavelength may e.g. be determined at operation conditions.

As indicated, with such light some bacteria and/or some virus may be inactivated. The efficacy of such first light generating device, however, may be relatively low due to the short wavelength, whereas the eye is much more sensitive in the green. Further, it appears that the outcoupling of the first light source light via a light transmissive material, may be lower than desired. Embedding of some (first) luminescent material in the light transmissive material provides a better outcoupling. It appears that a relatively low amount and a relatively low conversion may already have desirable effects. Hence, with a relatively low conversion, leaving a substantial contribution of the original short wavelength radiation, a type of white light may be generated, which may (nevertheless) have useful properties for reducing viral load and/or bacterial load.

Hence, the first light generating device may comprise a (first) luminescent material. The first converter light may in embodiments essentially be provided by the first luminescent material. The first converter may comprise one or more (first) luminescent materials.

Below, some embodiments in relation to luminescent materials are described, which may relate to the first luminescent material (of the first light generating device) and/or the (optional) second luminescent material (of the second light generating device).

The term "luminescent material" especially refers to a material that can convert first radiation, especially one or more of UV radiation and blue radiation, into second radiation. In general, the first radiation and second radiation have different spectral power distributions. Hence, instead of the term "luminescent material", also the terms "luminescent converter" or "converter" may be applied. In general, the second radiation has a spectral power distribution at larger wavelengths than the first radiation, which is the case in the so-called down-conversion. In specific embodiments, however the second radiation has a spectral power distribution with intensity at smaller wavelengths than the first radiation, which is the case in the so-called up-conversion.

In embodiments, the "luminescent material" may especially refer to a material that can convert radiation into e.g. visible and/or infrared light. For instance, in embodiments the luminescent material may be able to convert one or more of UV radiation and blue radiation, into visible light. The luminescent material may in specific embodiments also convert radiation into infrared radiation (IR). Hence, upon excitation with radiation, the luminescent material emits radiation. In general, the luminescent material will be a down converter, i.e. radiation of a smaller wavelength is converted into radiation with a larger wavelength ($\lambda_{ex} < \lambda_{em}$), though in specific embodiments the luminescent material may comprise up-converter luminescent material, i.e. radiation of a larger wavelength is converted into radiation with a smaller wavelength ($\lambda_{ex} > \lambda_{em}$).

In embodiments, the term "luminescence" may refer to phosphorescence. In embodiments, the term "luminescence" may also refer to fluorescence. Instead of the term "luminescence", also the term "emission" may be applied. Hence, the terms "first radiation" and "second radiation" may refer to excitation radiation and emission (radiation), respectively. Likewise, the term "luminescent material" may in embodiments refer to phosphorescence and/or fluorescence.

The term "luminescent material" may also refer to a plurality of different luminescent materials. Examples of possible luminescent materials are indicated below. Hence, the term "luminescent material" may in specific embodiments also refer to a luminescent material composition.

In embodiments, luminescent materials are selected from garnets and nitrides, especially doped with trivalent cerium or divalent europium, respectively. The term "nitride" may also refer to oxynitride or nitridosilicate, etc. Alternatively or additionally, the luminescent material(s) may be selected from silicates, especially doped with divalent europium.

In specific embodiments the luminescent material comprises a luminescent material of the type $A_3B_5O_{12}$:Ce, wherein A in embodiments comprises one or more of Y, La, Gd, Tb and Lu, especially (at least) one or more of Y, Gd, Tb and Lu, and wherein B in embodiments comprises one or more of Al, Ga, In and Sc. Especially, A may comprise one or more of Y, Gd and Lu, such as especially one or more of Y and Lu. Especially, B may comprise one or more of Al and Ga, more especially at least Al, such as essentially entirely Al. Hence, especially suitable luminescent materials are cerium comprising garnet materials. Embodiments of garnets especially include $A_3B_5O_{12}$ garnets, wherein A comprises at least yttrium or lutetium and wherein B comprises at least aluminum. Such garnets may be doped with cerium (Ce), with praseodymium (Pr) or a combination of cerium and praseodymium; especially however with Ce. Especially, B may comprise aluminum (Al); however, in addition to aluminum, B may also partly comprise gallium (Ga) and/or scandium (Sc) and/or indium (In), especially up to about 20% of B, more especially up to about 10% of B (i.e. the B ions essentially consist of 90 or more mole % of Al and 10 or less mole % of one or more of Ga, Sc, and In); B may especially comprise up to about 10% gallium. In another variant, B and O may at least partly be replaced by Si and N. The element A may especially be selected from the group consisting of yttrium (Y), gadolinium (Gd), terbium (Tb) and lutetium (Lu). Further, Gd and/or Tb are especially only present up to an amount of about 20% of A. In a specific embodiment, the garnet luminescent material comprises $(Y_{1-x}Lu_x)_3B_5O_{12}$:Ce, wherein x is equal to or larger than 0 and equal to or smaller than 1. The term ":Ce", indicates that part of the metal ions (i.e. in the garnets: part of the "A" ions) in the luminescent material is replaced by Ce. For instance, in the case of $(Y_{1-x}Lu_x)_3Al_5O_{12}$:Ce, part of Y and/or Lu is replaced by Ce. This is known to the person skilled in the art. Ce will replace A in general for not more than 10%; in general, the Ce concentration will be in the range of 0.1 to 4%, especially 0.1 to 2% (relative to A). Assuming 1% Ce and 10% Y, the full correct formula could be $(Y_{0.1}Lu_{0.89}Ce_{0.01})_3Al_5O_{12}$. Ce in garnets is substantially or only in the trivalent state, as is known to the person skilled in the art.

In embodiments, the luminescent material (thus) comprises $A_3B_5O_{12}$ wherein in specific embodiments at maximum 10% of B—O may be replaced by Si—N.

In specific embodiments the luminescent material comprises $(Y_{x1-x2\ x3}A'_{x2}Ce_{x3})_3(Al_{y1-y2}B'_{y2})_5O_{12}$, wherein x1+x2+x3=1, wherein x3>0, wherein 0<x2+x3≤0.2, wherein y1+y2=1, wherein 0≤y2≤0.2, wherein A' comprises one or more elements selected from the group consisting of lanthanides, and wherein B' comprises one or more elements selected from the group consisting of Ga, In and Sc. In embodiments, x3 is selected from the range of 0.001-0.1. In the present invention, especially x1>0, such as >0.2, like at least 0.8. Garnets with Y may provide suitable spectral power distributions.

In specific embodiments at maximum 10% of B—O may be replaced by Si—N. Here, B in B—O refers to one or more of Al, Ga, In and Sc (and O refers to oxygen); in specific embodiments B—O may refer to Al—O. As indicated above, in specific embodiments x3 may be selected from the range of 0.001-0.04. Especially, such luminescent materials may have a suitable spectral distribution (see however below), have a relatively high efficiency, have a relatively high thermal stability, and allow a high CRI (optionally in combination with (the) light of other sources of light as described herein). Hence, in specific embodiments A may be selected from the group consisting of Lu and Gd. Alternatively or additionally, B may comprise Ga. Hence, in embodiments the luminescent material comprises $(Y_{x1-x2-x3}(Lu,Gd)_{x2}Ce_{x3})_3(Al_{y1-y2}Ga_{y2})_5O_{12}$, wherein Lu and/or Gd may be available. Even more especially, x3 is selected from the range of 0.001-0.1, wherein 0<x2+x3≤0.1, and wherein 0≤y2≤0.1. Further, in specific embodiments, at maximum 1% of B—O may be replaced by Si—N. Here, the percentage refers to moles (as known in the art); see e.g. also EP3149108. In yet further specific embodiments, the luminescent material comprises $(Y_{x1-x3}Ce_{x3})_3Al_5O_{12}$, wherein $x1+x3=1$, and wherein $0<x3\leq0.2$, such as 0.001-0.1.

In specific embodiments, the light generating device may only include luminescent materials selected from the type of cerium comprising garnets. In even further specific embodiments, the light generating device includes a single type of luminescent materials, such as $(Y_{x1-x2-x3}A'_{x2}Ce_{x3})_3(Al_{y1-y2}B'_{y2})_5O_{12}$. Hence, in specific embodiments the light generating device comprises luminescent material, wherein at least 85 weight %, even more especially at least about 90 wt. %, such as yet even more especially at least about 95 weight % of the luminescent material comprises $(Y_{x1-x2-x3}A'_{x2}Ce_{x3})_3(Al_{y1-y2}B'_{y2})_5O_{12}$. Here, wherein A' comprises one or more elements selected from the group consisting of lanthanides, and wherein B' comprises one or more elements selected from the group consisting of Ga, In and Sc, wherein $x1+x2+x3=1$, wherein $x3>0$, wherein $0<x2+x3\leq0.2$, wherein $y1+y2=1$, wherein $0\leq y2\leq0.2$. Especially, x3 is selected from the range of 0.001-0.1. Note that in embodiments $x2=0$. Alternatively or additionally, in embodiments $y2=0$.

In specific embodiments, A may especially comprise at least Y, and B may especially comprise at least Al.

Alternatively or additionally, wherein the luminescent material may comprise a luminescent material of the type $A_3Si_6N_{11}:Ce^{3+}$, wherein A comprises one or more of Y, La, Gd, Tb and Lu, such as in embodiments one or more of La and Y.

In embodiments, the luminescent material may alternatively or additionally comprise one or more of $MS:Eu^{2+}$ and/or $M_2Si_5N_8:Eu^{2+}$ and/or $MAlSiN_3:Eu^{2+}$ and/or $Ca_2AlSi_3O_2N_5:Eu^{2+}$, etc., wherein M comprises one or more of Ba, Sr, and Ca, especially in embodiments at least Sr. Hence, in embodiments, the luminescent may comprise one or more materials selected from the group consisting of (Ba,Sr,Ca)S:Eu, (Ba,Sr,Ca)AlSiN$_3$:Eu and (Ba,Sr,Ca)$_2$Si$_5$N$_8$:Eu. In these compounds, europium (Eu) is substantially or only divalent, and replaces one or more of the indicated divalent cations. In general, Eu will not be present in amounts larger than 10% of the cation; its presence will especially be in the range of about 0.5 to 10%, more especially in the range of about 0.5 to 5% relative to the cation(s) it replaces. The term ":Eu", indicates that part of the metal ions is replaced by Eu (in these examples by $Eu^{2+}$). For instance, assuming 2% Eu in CaAlSiN$_3$:Eu, the correct formula could be $(Ca_{0.98}Eu_{0.02})AlSiN_3$. Divalent europium will in general replace divalent cations, such as the above divalent alkaline earth cations, especially Ca, Sr, or Ba. The material (Ba,Sr,Ca)S:Eu can also be indicated as MS:Eu, wherein M is one or more elements selected from the group consisting of barium (Ba), strontium (Sr) and calcium (Ca); especially, M comprises in this compound calcium or strontium, or calcium and strontium, more especially calcium. Here, Eu is introduced and replaces at least part of M (i.e. one or more of Ba, Sr, and Ca). Further, the material (Ba,Sr,Ca)$_2$Si$_5$N$_8$:Eu can also be indicated as M$_2$Si$_5$N$_8$:Eu, wherein M is one or more elements selected from the group consisting of barium (Ba), strontium (Sr) and calcium (Ca); especially, M comprises in this compound Sr and/or Ba. In a further specific embodiment, M consists of Sr and/or Ba (not taking into account the presence of Eu), especially 50 to 100%, more especially 50 to 90% Ba and 50 to 0%, especially 50 to 10% Sr, such as $Ba_{1.5}Sr_{0.5}Si_5N_8$:Eu (i.e. 75% Ba; 25% Sr). Here, Eu is introduced and replaces at least part of M, i.e. one or more of Ba, Sr, and Ca). Likewise, the material (Ba,Sr,Ca)AlSiN$_3$:Eu can also be indicated as MAlSiN$_3$:Eu, wherein M is one or more elements selected from the group consisting of barium (Ba), strontium (Sr) and calcium (Ca); especially, M comprises in this compound calcium or strontium, or calcium and strontium, more especially calcium. Here, Eu is introduced and replaces at least part of M (i.e. one or more of Ba, Sr, and Ca). Eu in the above indicated luminescent materials is substantially or only in the divalent state, as is known to the person skilled in the art.

In embodiments, a red luminescent material may comprise one or more materials selected from the group consisting of (Ba,Sr,Ca)S:Eu, (Ba,Sr,Ca)AlSiN$_3$:Eu and (Ba,Sr,Ca)$_2$Si$_5$N$_8$:Eu. In these compounds, europium (Eu) is substantially or only divalent, and replaces one or more of the indicated divalent cations. In general, Eu will not be present in amounts larger than 10% of the cation; its presence will especially be in the range of about 0.5 to 10%, more especially in the range of about 0.5 to 5% relative to the cation(s) it replaces. The term ":Eu", indicates that part of the metal ions is replaced by Eu (in these examples by $Eu^{2+}$). For instance, assuming 2% Eu in CaAlSiN$_3$:Eu, the correct formula could be $(Ca_{0.98}Eu_{0.02})AlSiN_3$. Divalent europium will in general replace divalent cations, such as the above divalent alkaline earth cations, especially Ca, Sr or Ba.

The material (Ba,Sr,Ca)S:Eu can also be indicated as MS:Eu, wherein M is one or more elements selected from the group consisting of barium (Ba), strontium (Sr) and calcium (Ca); especially, M comprises in this compound calcium or strontium, or calcium and strontium, more especially calcium. Here, Eu is introduced and replaces at least part of M (i.e. one or more of Ba, Sr, and Ca).

Further, the material (Ba,Sr,Ca)$_2$Si$_5$N$_8$:Eu can also be indicated as M$_2$Si$_5$N$_8$:Eu, wherein M is one or more elements selected from the group consisting of barium (Ba), strontium (Sr) and calcium (Ca); especially, M comprises in this compound Sr and/or Ba. In a further specific embodiment, M consists of Sr and/or Ba (not taking into account the presence of Eu), especially 50 to 100%, more especially 50 to 90% Ba and 50 to 0%, especially 50 to 10% Sr, such as $Ba_{1.5}Sr_{0.5}Si_5N_8$:Eu (i.e. 75% Ba; 25% Sr). Here, Eu is introduced and replaces at least part of M, i.e. one or more of Ba, Sr, and Ca).

Likewise, the material (Ba,Sr,Ca)AlSiN$_3$:Eu can also be indicated as MAlSiN$_3$:Eu, wherein M is one or more elements selected from the group consisting of barium (Ba), strontium (Sr) and calcium (Ca); especially, M comprises in this compound calcium or strontium, or calcium and strontium, more especially calcium. Here, Eu is introduced and replaces at least part of M (i.e. one or more of Ba, Sr, and Ca).

Eu in the above indicated luminescent materials is substantially or only in the divalent state, as is known to the person skilled in the art.

Blue luminescent materials may comprise YSO ($Y_2SiO_5$:$Ce^{3+}$), or similar compounds, or BAM ($BaMgAl_{10}mO_{17}$:$Eu^{2+}$), or similar compounds.

The term "luminescent material" herein especially relates to inorganic luminescent materials.

Instead of the term "luminescent material" also the term "phosphor". These terms are known to the person skilled in the art.

Alternatively or additionally, also other luminescent materials may be applied. For instance quantum dots and/or organic dyes may be applied and may optionally be embedded in transmissive matrices like e.g. polymers, like PMMA, or polysiloxanes, etc. etc.

Quantum dots are small crystals of semiconducting material generally having a width or diameter of only a few nanometers. When excited by incident light, a quantum dot emits light of a color determined by the size and material of the crystal. Light of a particular color can therefore be produced by adapting the size of the dots. Most known quantum dots with emission in the visible range are based on cadmium selenide (CdSe) with a shell such as cadmium sulfide (CdS) and zinc sulfide (ZnS). Cadmium free quantum dots such as indium phosphide (InP), and copper indium sulfide ($CuInS_2$) and/or silver indium sulfide ($AgInS_2$) can also be used. Quantum dots show very narrow emission band and thus they show saturated colors. Furthermore the emission color can easily be tuned by adapting the size of the quantum dots. Any type of quantum dot known in the art may be used in the present invention. However, it may be preferred for reasons of environmental safety and concern to use cadmium-free quantum dots or at least quantum dots having a very low cadmium content.

Instead of quantum dots or in addition to quantum dots, also other quantum confinement structures may be used. The term "quantum confinement structures" should, in the context of the present application, be understood as e.g. quantum wells, quantum dots, quantum rods, tripods, tetrapods, or nano-wires, etcetera.

Organic phosphors can be used as well. Examples of suitable organic phosphor materials are organic luminescent materials based on perylene derivatives, for example compounds sold under the name Lumogen® by BASF. Examples of suitable compounds include, but are not limited to, Lumogen® Red F305, Lumogen® Orange F240, Lumogen® Yellow F083, and Lumogen® F170.

Different luminescent materials may have different spectral power distributions of the respective luminescent material light. Alternatively or additionally, such different luminescent materials may especially have different color points (or dominant wavelengths).

As indicated above, other luminescent materials may also be possible. Hence, in specific embodiments the luminescent material is selected from the group of divalent europium containing nitrides, divalent europium containing oxynitrides, divalent europium containing silicates, cerium comprising garnets, and quantum structures. Quantum structures may e.g. comprise quantum dots or quantum rods (or other quantum type particles) (see above). Quantum structures may also comprise quantum wells. Quantum structures may also comprise photonic crystals.

Especially, the first luminescent material may provide a broad band emission.

The luminescent material may be chosen such that an emission band of a full width half maximum (of the luminescent material light) of at least 40 nm, such as at least 50 nm is obtained. For instance, the luminescent material may be chosen such that an emission band of a full width half maximum of at least 60 nm, is obtained. This may e.g. be the case with trivalent cerium comprising garnet luminescent materials (as described herein). Hence, especially the luminescent material may comprise a broad band emitter. The luminescent material may also comprise a plurality of broad band emitters. Especially, when two or more luminescent materials are applied to convert at least part of the first device light and/or at least part of the second device light, at least two of the two or more luminescent materials may be configured to provide respective luminescent material light each having an emission band with full width half maximum (of the luminescent material light) of at least 40 nm, such as at least 50 nm.

In specific embodiments, the first luminescent converter may be configured to convert (at least) part of the first light source light into first converter light. Further, in embodiments the first converter light may have a first converter centroid wavelength ($\lambda_{c,1}$). Especially, the first converter centroid wavelength ($\lambda_{c,1}$) selected from the green-yellow wavelength range. Hence, the first converter centroid wavelength ($\lambda_{c,1}$) may be within the 490-590 nm wavelength range, especially at least 500 nm, and especially at maximum about 580 nm.

The terms "violet light" or "violet emission", and similar terms, especially relate to light having a wavelength in the range of about 380-440 nm. In specific embodiments, the violet light may have a centroid wavelength in the 380-440 nm range. The terms "blue light" or "blue emission", and similar terms, especially relate to light having a wavelength in the range of about 440-490 nm (including some violet and cyan hues). In specific embodiments, the blue light may have a centroid wavelength in the 440-490 nm range. The terms "green light" or "green emission", and similar terms, especially relate to light having a wavelength in the range of about 490-560 nm. In specific embodiments, the green light may have a centroid wavelength in the 490-560 nm range. The terms "yellow light" or "yellow emission", and similar terms, especially relate to light having a wavelength in the range of about 560-590 nm. In specific embodiments, the yellow light may have a centroid wavelength in the 560-590 nm range. The terms "orange light" or "orange emission", and similar terms, especially relate to light having a wavelength in the range of about 590-620 nm. In specific embodiments, the orange light may have a centroid wavelength in the 590-620 nm range. The terms "red light" or "red emission", and similar terms, especially relate to light having a wavelength in the range of about 620-750 nm. In specific embodiments, the red light may have a centroid wavelength in the 620-750 nm range. The term "cyan light" or "cyan emission", and similar terms, especially relate to light having a wavelength in the range of about 490-520 nm. In specific embodiments, the cyan light may have a centroid wavelength in the 490-520 nm range. The term "amber light" or "amber emission", and similar terms, especially relate to light having a wavelength in the range of about 585-605 nm, such as about 590-600 nm. In specific embodiments, the amber light may have a centroid wavelength in the 585-605 nm range.

In this way, the first light generating device may especially be configured to generate first device light comprising the first light source light and the first converter light. Especially, the first device light may essentially consist of the first light source light and the first converter light, with the latter essentially being generated by the one or more first (solid state) light sources, and the latter being generated by conversion of part of the first light source light into the first converter light. In specific embodiments, relative to a spectral power distribution of first device light in the range of 380-780 nm, at least 60% of the spectral power may be provided by the first light source light and at maximum 40% of the spectral power may be provided by the first converter light.

In specific embodiments, the first luminescent converter may comprise a first matrix material and a first luminescent material. Examples of first luminescent material are given above and below, with special attention to those that may provide essentially green and/or yellow light. Hence, in embodiments the first luminescent converter may be configured to convert the first light source light into first converter light having the first converter centroid wavelength ($\lambda_{c,1}$) selected from the yellow-green wavelength range, even more especially from the green wavelength range.

In specific embodiments, relative to a spectral power distribution of the first converter light in the range of 380-780 nm, at maximum 20% of the spectral power may be within the range of 585-780 nm. Hence, the intensity in the orange-red wavelength range of the spectral power distribution of the first converter light may be relatively low. Therefore, the first converter light may have a spectral power distribution in the 380-780 nm wavelength range, wherein at maximum 20% of the spectral power in that wavelength range is available in the 585-780 nm wavelength range.

The matrix material may especially comprise a resin, such as a silicone.

In specific embodiments, the first luminescent material has a first weight percentage CW1 relative to the total weight of the first luminescent converter. In embodiments, CW1≤10 wt %, such as selected from the range of about 0.1-10 wt %, such as selected from the range of about 0.5-8 weight %.

In specific embodiments, the first luminescent material has a first volume percentage CVl relative to the total volume of the first luminescent converter. In embodiments, CV1≤3 vol %, such as selected from the range of about 0.03-3 vol. %, such as selected from the range of about 0.15-2.5 volume %.

In embodiments, the first device light may have a relatively high correlated color temperature (CCT). Especially, the CCT of the first device light may be in embodiments at least about 5500 K, like at least 6000 K. In specific embodiments, the first device light may have a correlated color temperature selected from the range of 6000-25000 K. In specific embodiments, the first device light may have a correlated color temperature selected from the range of at least about 6500 K. The first device light may be relatively cool white light, or cool whitish light. In specific embodiments, the first device light may have a color point selected within 0-20 SDCM from the black body locus (BBL), such as within about 15 SDCM from the BBL, like within about 10 SDCM. Hence, the first device light may be whitish.

However, the first device light may in other embodiments also be substantially offset from the BBL, such as with a color point at (substantially) more than 20 SDCM from the BBL.

In embodiments, the first device light may have a color point wherein u' is selected from the range of 0.10-0.22 and wherein v' is selected from the range of 0.25-0.55. More especially, in specific embodiments, the first device light may have a color point with u' is selected from the range of 0.12-0.22, such as 0.12-0.20, and with v' is selected from the range of 0.30-0.50. In such embodiments, the first device light may be relatively offset from the BBL. In combination with the second device light, color points may be generated in the white, and within 0-20 SDCM from the black body locus (BBL), such as within about 15 SDCM from the BBL, like within about 10 SDCM.

In embodiments, the first device light may have a color which may be blueish or cyan-like.

In specific embodiments, the first converter light may have a first spectral power distribution in the 380-780 nm wavelength range, with at maximum 15% of its spectral power in the wavelength range of 380-490 nm, such as at maximum 10%. Hence, the first luminescent material(s) may have substantially no blue emission (and in specific embodiments essentially green and/or yellow).

The term white light, and similar terms, herein, is known to the person skilled in the art. It especially relates to light having a correlated color temperature (CCT) between about 1800 K and 20000 K, like at least about 2000 K, especially in the range of 2700-20000 K, for general lighting especially in the range of about 2000-6700 K, such as 2700-6500 K, and for backlighting purposes especially in the range of about 6500 K and 20000 K, and especially within about 15 SDCM (standard deviation of color matching) from the BBL (black body locus), especially within about 10 SDCM from the BBL, even more especially within about 5 SDCM from the BBL.

In embodiments, the first device light may have a color rendering index of at maximum about 80, such as at maximum about 70, such as even lower, like at maximum about 60. In embodiments, the first device light may even not be white or whitish light.

Especially, the first light generating device may be provided in combination with a second light generating device. The latter may be configured to generate white light, whereas the former's function is essentially to provide the disinfection light having a wavelength selected from the 380-430 nm, such as 380-425 nm, more especially 380-420 nm wavelength range, more especially from the range of 395-415 nm, yet even more especially selected from the range of 400-410 nm.

In specific embodiments, the first light generating device may be configured to generate first device light having a spectral power distribution in the wavelength range of 380-780 nm with at least 70% of the spectral power provided by the first light source light and at maximum 30% of the spectral power provided by the first converter light. In embodiments, the spectral power distribution of the first device light may comprise in the range of 70-90% of the spectral power provided by the first light source light and in the range of 10-30% of the spectral power provided by the first converter light.

In specific embodiments, the first light generating device may be configured to generate first device light having a spectral power distribution in the wavelength range of 380-780 nm with at least 70% of the spectral power provided by the first light source light and at maximum 30% of the spectral power provided by the first converter light. More especially, the first light generating device may be configured to generate first device light having a spectral power distribution in the wavelength range of 380-780 nm with at least 75% of the spectral power provided by the first light source light and at maximum 25% of the spectral power provided by the first converter light. Yet, especially in embodiments the first light generating device may be configured to generate first device light having a spectral power distribution in the wavelength range of 380-780 nm with at least 80% of the spectral power provided by the first light source light and at maximum 20% of the spectral power provided by the first converter light.

In specific embodiments, the first light generating device may be configured to generate first device light having a spectral power distribution in the wavelength range of 380-780 nm with at maximum 98% of the spectral power provided by the first light source light and at least 2% of the spectral power provided by the first converter light. More especially, the first light generating device may be configured to generate first device light having a spectral power distribution in the wavelength range of 380-780 nm with at maximum 96% of the spectral power provided by the first light source light and at least 4% of the spectral power provided by the first converter light. Yet, especially in embodiments the first light generating device may be configured to generate first device light having a spectral power distribution in the wavelength range of 380-780 nm with at maximum 95% of the spectral power provided by the first light source light and at least 5% of the spectral power provided by the first converter light.

The phrase "spectral power distribution in the wavelength range of 380-780 nm", and similar phrases herein, especially refer to a spectral power distribution defined in this range. Alternatively, the phrase "spectral power distribution in the visible wavelength range", and similar phrases, may be applied. Light having a spectral power distribution in the visible may in specific embodiments also have intensity in the UV or IR. Herein, however, it is in general only referred to the visible. Light having intensity in the visible may have an intensity at one or more wavelengths in the visible wavelength range.

The terms "visible", "visible light" or "visible emission" and similar terms refer to light having one or more wavelengths in the range of about 380-780 nm. Herein, UV may especially refer to a wavelength selected from the range of 190-380 nm, such as 200-380 nm.

The terms "light" and "radiation" are herein interchangeably used, unless clear from the context that the term "light" only refers to visible light. The terms "light" and "radiation" may thus refer to UV radiation, visible light, and IR radiation. In specific embodiments, especially for lighting applications, the terms "light" and "radiation" refer to (at least) visible light.

The first light generating device may be provided as LED package.

As indicated above, the light generating system may comprise a second light generating device. Further, as indicated above, especially, the term "light generating device" may refer to a device comprising a solid state light source, like a light emitting diode (LED).

The term "second light generating device" may also refer to a plurality of second light generating devices, of which two or more may be same and/or of which two or more may be different. Especially, the second light generating device may comprise a second light source and a second luminescent converter.

In embodiments, the second light source may comprise a solid state light source. Further, as indicated above, the term "second light source" may also refer to a plurality of second light sources, of which two or more may be same and/or of which two or more may be different. Especially, the second light source comprises a solid state light source, like a laser diode or a LED, especially a LED. Especially, when there are more than one second light sources, the second light sources may be of the same bin.

In embodiments, the second light source may be configured to generate second light source light having a wavelength selected from the 440-490 nm wavelength range, more especially from the range of 440-485 nm, yet even more especially selected from the range of 445-480 nm. More especially, the second light source may be configured to generate second light source light having a peak wavelength selected from the 440-490 nm wavelength range, more especially from the range of 440-485 nm, yet even more especially selected from the range of 445-480 nm.

Yet, in embodiments, the second light source may be configured to generate second light source light having a second light source centroid wavelength ($\lambda_{s,1}$) selected from the range of 440-490 nm. More especially, the second light source centroid wavelength ($\lambda_{s,1}$) may be selected from the range of 440-485 nm. Especially, wavelength around about 450-460 nm may be suitable. Hence, in further specific embodiments the second light source centroid wavelength ($k_{s,1}$) may be selected from the range of 445-480 nm.

Hence, in embodiments the light generating system may further comprise a second light generating device. Especially, the second light generating device may comprise a second light source and a second luminescent converter. In embodiments, the second light source may comprise a solid state light source. Especially, the second light source may be configured to generate second light source light. In further specific embodiments, the second light source light may have a second light source centroid wavelength ($\lambda_{s,2}$) selected from the range of 440-490 nm.

Hence, especially in embodiments $\lambda_{s,2} \neq \lambda_{s,1}$. Especially, in embodiments $\lambda_{s,2} - \lambda_{s,1} > 20$ nm, even more especially $\lambda_{s,2} - \lambda_{s,1} \geq 30$ nm, such as $\lambda_{s,2} - \lambda s, 1 \geq 35$ nm. Especially, in embodiments $\lambda_{s,2} - \lambda_{s,1} \leq 90$ nm, such as $\lambda_{s,2} - \lambda_{s,1} \leq 80$ nm, like in embodiments $\lambda_{s,2} - \lambda_{s,1} \leq 75$ nm.

Especially, the second luminescent converter may be configured to convert at least part of the second light source light into second converter light. In yet further specific embodiments, the second luminescent converter light may have a second converter centroid wavelength ($\lambda_{c,2}$) selected from the green-red wavelength range, i.e. from the wavelength range of 490-780 nm (and thus also including e.g. yellow and orange).

Hence, the second light generating device may comprise a (second) luminescent material. The second converter light may in embodiments essentially be provided by the second luminescent material. The second converter may comprise one or more (second) luminescent materials.

Especially, the second converter may comprise two different luminescent materials, like one having a centroid wavelength range in the green-yellow, and another one having a centroid wavelength in the orange-red wavelength range.

Especially, the second luminescent material may provide a broad band emission.

In this way, the second light generating device may especially be configured to generate second device light comprising the second light source light and the second converter light. Especially, the second device light may essentially consist of the second light source light and the second converter light, with the former essentially being generated by the one or more second (solid state) light sources, and the latter being generated by conversion of part of the second light source light into the second converter light.

In embodiments, the second light generating device may be configured to generate second device light having a spectral power distribution in the wavelength range of 380-780 nm with at least 50% of the spectral power provided by the second converter light and at maximum 50% of the spectral power provided by the second light source light, more especially at least 60% of the spectral power provided by the second converter light and at maximum 40% of the spectral power provided by the second light source light.

In specific embodiments, the second light generating device may be configured to generate second device light having a spectral power distribution in the wavelength range of 380-780 nm with at maximum 30% of the spectral power provided by the second light source light and at least 70% of the spectral power provided by the second converter light. In embodiments, the spectral power distribution of the second device light (in the wavelength range of 380-780 nm) may comprise in the range of 10-30% of the spectral power provided by the second light source light and in the range of 70-90% of the spectral power provided by the second converter light.

Hence, the second device light may essentially consist of the second light source light and second converter light.

Especially, in embodiments the second luminescent converter may be configured to convert the second light source light into second converter light having the second converter centroid wavelength ($\lambda_{c,2}$) selected from green-red wavelength range.

In specific embodiments, the second luminescent converter may comprise a second matrix material and a second luminescent material. Examples of second luminescent material are given above and below, with special attention to those that may provide essentially one or more, especially two or more of green, yellow, orange, and red light. The matrix material may especially comprise a resin, such as a silicone.

In specific embodiments, the second luminescent material may have a second weight percentage CW2 relative to the total weight of the second luminescent converter. In embodiments, CW2≥10 wt %, such as selected from the range of about 10-70 wt %, such as at least about 20 wt %, like selected from the range of about 20-70 weight %, such as in specific embodiments selected from the range of about 50-70 weight %.

In specific embodiments, the second luminescent material has a second volume percentage CV2 relative to the total volume of the second luminescent converter. In embodiments, CV2≥3 vol %, such as selected from the range of about 3-23 vol. %, such as selected from the range of about 6-20 volume %.

Especially, the second light generating device may be configured to generate second device light comprising the second converter light and the second light source light. More especially, the second device light may be white light.

As will be clear from the above, especially the first device light spectral power distribution of the first device light and a second device light spectral power distribution of the second device light differ. Further, they may have different color points, though the color point difference may depend upon the desired CCT of the second device light. Would the CCT of the second device light be relatively high, then the color point difference between the first device light and second device light may be smaller than when the CCT of the second device light would be relatively low.

In specific embodiments, colors or color points of a first type of light and a second type of light may be different when the respective color points of the first type of light and the second type of light differ with at least 0.01 for u' and/or with at least 0.01 for v', even more especially at least 0.02 for u' and/or with at least 0.02 for v'. In yet more specific embodiments, the respective color points of first type of light and the second type of light may differ with at least 0.03 for u' and/or with at least 0.03 for v'. Here, u' and v' are color coordinate of the light in the CIE 1976 UCS (uniform chromaticity scale) diagram.

In embodiments, the difference in u' and/or v' between the first device light and the second device light may be at least 0.03, such as in further specific embodiments at least 0.05.

In specific embodiments, the second light source centroid wavelength ($\lambda_{s,2}$) may be selected from the range of 445-480 nm.

The second device light may have a lower correlated color temperature (CCT) than the first device light. Especially, the CCT of the second device light may be in embodiments at maximum about 6500 K, like at maximum 6000 K (though larger is herein not excluded). In specific embodiments, the second device light may have a correlated color temperature selected from the range of 1800-6500 K. In specific embodiments, the second device light may have a correlated color temperature selected from the range of at maximum about 4500 K, such as selected from the range of 2000-4500 K, like selected from the range of about 2700-4000 K. However, other values may also be possible. The second device light may be warm white light, though this is not necessarily the case. In specific embodiments, the second device light may have a color point selected within 0-20 SDCM from the black body locus (BBL), such as within about 15 SDCM from the BBL, like within about 10 SDCM. In embodiments, the second device light may have a color rendering index of at minimum 70, such as at least about 75, like at least about 80, or even at least 85, and in specific embodiments at least about 90.

Therefore, in specific the second device light may have a correlated color temperature selected from the range of 1800-6500 K, such as selected from the range of 2000-4500 K, and a (second device light) color point within 0-15 SDCM from the black body locus, and a color rendering index of at minimum 70, such as at least about 75, like at least about 80. However, higher values, like at least about 85 may also be possible. Yet, in specific embodiments the second device light may have a CRI of at least 90.

The second light generating device may be provided as LED package.

When using a host material for the luminescent materials, such as a resin, the weight percentage of first luminescent material in the first luminescent converter may be lower than the weight percentage of the second luminescent material in the second luminescent converter. The contribution of the first converter light in the first device light may (substantially) be lower than the contribution of the second converter light in the second device light. In specific embodiments, CW1/CW2≤0.5, such as more especially CW1/CW2≤0.3.

With such system light bacteria and/or viruses can be inactivated very well. The reason is that the outcoupling of the first light source light is (relatively) high. Surprisingly, it appears that a relatively low amount of first luminescent material and relatively low conversion may already have desirable effects. Hence, with a relatively low conversion, such a configuration leaves a substantial contribution of the original short wavelength radiation (380-420 nm).

Further, in embodiments the first luminescent material may have a first volume percentage CV1 of first luminescent material in the first luminescent converter and the second luminescent material may have a second volume percentage CV2 of the second luminescent material in the second luminescent converter. Especially, CV1/CV2≤0.5, more especially CV1/CV2≤0.3.

In embodiments, the first luminescent material may comprise particulate material. This may be useful for outcoupling of the first light source light. Further, in embodiments the first matrix material may comprise a resin, such as especially a silicone resin.

In embodiments, the second luminescent material may comprise particulate material. The second matrix material may comprise a resin, especially a silicone resin. In embodiments, the resins may be the same. In other embodiments, they may be different.

In specific embodiments, at least 50 wt % of the first luminescent material has a particle dimension selected from the range of 1-20 μm. The particle dimension may be selected from length, width, height, diameter, or spherical equivalent diameter (or equivalent spherical diameter). The equivalent spherical diameter (or ESD) of an (irregularly) shaped object is the diameter of a sphere of equivalent volume. Hence, the equivalent spherical diameter (ESD) of a cube with a side a is $2*a*3\sqrt{3}(4*\pi)$. Would a sphere in an xyz-coordinate system with a diameter D be distorted to any other shape (in the xyz-plane), without changing the volume, than the equivalent spherical diameter of that shape would be D.

Particle sizes may be determined with methods known in the art, like one or more of optical microscopy, SEM (scanning electron microscope) and TEM (transmission electron microscopy). Dimensions may be number averaged, as known in the art. Hence, the particles may be substantially identical, but the particles may also mutually differ, such as two or more subsets of particles, wherein within the subsets the particles are substantially identical. The particles may have a unimodal particle size distribution or a polymodal size distribution. In further embodiments, a d50 value of the first luminescent material may be selected from the range of 1-20 μm. A d50 value may be determined with methods known in the art, like laser scattering of the luminescent material that is used for the luminescent converter.

In specific embodiments, at least 50 wt % of the second luminescent material may have a particle dimension selected from the range of 1-20 μm. The particle dimension may be selected from length, width, height, diameter, or spherical equivalent diameter (or equivalent spherical diameter). In further embodiments, a d50 value of the second luminescent material may be selected from the range of 1-20 μm.

In embodiments, the first luminescent material may comprise a $Eu^{2+}$-based luminescent material. Such luminescent materials may have a better absorption in the low wavelength range, such as in the wavelength range of 380-430 nm, more especially 380-420 nm. In embodiments, the first luminescent material may comprise a $Ce^{3+}$-based luminescent material. Such materials may absorb more at the longer wavelength range of the first light source light emission band than at the shorter wavelength range, which may also be beneficial.

In embodiments, the first luminescent material may comprise one or more of:
Garnets, such as $(Lu_{1-x-y-a-b}Y_xGd_y)_3(Al_{1-z-u}Ga_zSi_u)_5O_{12-u}N_u:Ce_aPr_b$ wherein $0 \le x \le 1, 0 \le y \le 1, 0 < z \le 0.1, 0 \le u \le 0.2, 0 < a \le 0.2$ and $0 \le b \le 0.1$, such as $Lu_3Al_5O_{12}:Ce^{3+}$ and $Y_3Al_5O_{12}:Ce^{3+}$
Narrow green phosphor, such as $Ca_8Mg(SiO_4)_4Cl_2:Eu$
Silicon oxynitrides, such as $(Sr_{1-a-b-c}Ca_bBa_c)Si_xN_yO_z:Eua^{2+}$ wherein $a=0.002-0.2, b=0.0-0.25, c=0.0-1.0, x=1.5-2.5, y=0.67-2.5, z=1.5-4$ including, for example, $SrSi_2N_2O_2:Eu^{2+}$ and $BaSi_2N_{0.67}O_4:Eu^{2+}$
LSN, such as $(La,Y)Si_6N_{11}:Ce^{3+}$
Gallates, such as $(Sr_{1-u-v-x}Mg_uCa_vBa_x)(Ga_{2-y-z}Al_yIn_z S_4):Eu^{2+}$, wherein $0 \le u+v+x \le 1$ and $0 \le u+z \le 2$, including, for example, $SrGa_2S_4:Eu^{2+}$
Silicates, such as $(Sr_{1-x}Ba_x)_2SiO_4:Eu$, wherein $0 < x \le 1$, including, for example, $BaSrSiO_4:Eu^{2+}(Ca_{1-x-y-a-b}Y_xLu_y)_3(Sc_{1-z}Al_z)_2(Si_{1-x-y}Al_{x+y})_3O_{12}:Ce_aPr_b$ wherein $0 \le x \le 1, 0 \le y \le 1, 0 < z \le 1, 0 \le u \le 0.2, 0 \le a \le 0.2$ and $0 < b \le 0.1$, such as $Ca_3Sc_2Si_3O_{12}:Ce^{3+}$
$Ba_3Si_6O_{15-3x}N_{2x}$, wherein $0 \le x \le 5$, including for example $Ba_3Si_6O_{12}N_2:Eu^{2+}$
ß—SiAlON, such as $Si_{(6-z)}Al_zO_zN_{(8-z)}:Eu^{2+}$, wherein $0 \le z \le 6$.

In embodiments, the first luminescent material comprises a (trivalent) cerium comprising garnet luminescent material (such as comprising gallium and/or lutetium). Alternatively or additionally, the first luminescent material may comprise a (divalent) europium comprising luminescent material.

However, other luminescent materials are herein not excluded.

As indicated above, the system may be configured to generate system light. The system light may comprise one or more of the first device light and the second device light. Especially, in an operational mode the system light comprises both the first device light and the second device light. In embodiments, the system light may have a correlated color temperature selected from the range of 1800-6500 K. Further, in embodiments the system light may have a (system light) color point within 0-10 SDCM from the black body locus, and a color rendering index of at minimum 70, such as at least 80. In specific embodiments, the system light may have a CRI of at least 85.

In embodiments, the system light comprising the first device light and the second device light has a correlated color temperature which is at least 100 K, such as at least 200 K, like at least 500 K, such as in embodiments at least 1000 K higher than of the second device light. In specific embodiments, the difference in correlated color temperature between the second device light and the system light comprising the first device light and the second device light may be selected from the range of 500-15000 K, such as selected from the range of 500-10000 K.

In specific embodiments, the difference in u' between the second device light and the first device light comprised by the system light may be at least 0.02, even more especially at least 0.04. In specific embodiments, the difference in u' between the second device light and the first device light comprised by the system light may be selected from the range of 0.06-0.14.

In specific embodiments, the difference in v' between the second device light and the first device light comprised by the system light may be at least 0.01, even more especially at least 0.015. In specific embodiments, the difference in v' between the second device light and the first device light comprised by the system light may be selected from the range of 0.01-0.15.

As there are two types of light generating devices, it may be possible to control the system light. This may lead to different types of system light, which may differ in one or more of color point, correlated color temperature, and CRI.

Hence, in specific embodiments the light generating system may further comprising a control system. Especially, the control system may be configured to control the system light in dependence of one or more of an input signal of a user interface, a sensor signal (of a sensor), and a timer.

The term "controlling" and similar terms especially refer at least to determining the behavior or supervising the running of an element. Hence, herein "controlling" and similar terms may e.g. refer to imposing behavior to the element (determining the behavior or supervising the running of an element), etc., such as e.g. measuring, displaying, actuating, opening, shifting, changing temperature, etc.. Beyond that, the term "controlling" and similar terms may additionally include monitoring. Hence, the term "controlling" and similar terms may include imposing behavior on an element and also imposing behavior on an element and monitoring the element. The controlling of the element can be done with a control system, which may also be indicated as "controller". The control system and the element may thus at least temporarily, or permanently, functionally be coupled. The element may comprise the control system. In embodiments, the control system and element may not be physically coupled. Control can be done via wired and/or wireless control. The term "control system" may also refer to a plurality of different control systems, which especially are functionally coupled, and of which e.g. one control system may be a master control system and one or more others may be slave control systems. A control system may comprise or may be functionally coupled to a user interface.

The control system may also be configured to receive and execute instructions from a remote control. In embodiments, the control system may be controlled via an App on a device, such as a portable device, like a Smartphone or I-phone, a tablet, etc. The device is thus not necessarily coupled to the lighting system, but may be (temporarily) functionally coupled to the lighting system.

Hence, in embodiments the control system may (also) be configured to be controlled by an App on a remote device. In such embodiments the control system of the lighting system may be a slave control system or control in a slave mode. For instance, the lighting system may be identifiable with a code, especially a unique code for the respective lighting system. The control system of the lighting system may be configured to be controlled by an external control system which has access to the lighting system on the basis of knowledge (input by a user interface of with an optical sensor (e.g. QR code reader) of the (unique) code. The lighting system may also comprise means for communicating with other systems or devices, such as on the basis of Bluetooth, WIFI, LiFi, ZigBee, BLE or WiMAX, or another wireless technology.

The system, or apparatus, or device may execute an action in a "mode" or "operation mode" or "mode of operation" or "operational mode". The term "operational mode may also be indicated as "controlling mode". Likewise, in a method an action or stage, or step may be executed in a "mode" or "operation mode" or "mode of operation" or "operational mode". This does not exclude that the system, or apparatus, or device may also be adapted for providing another controlling mode, or a plurality of other controlling modes. Likewise, this may not exclude that before executing the mode and/or after executing the mode one or more other modes may be executed.

However, in embodiments a control system may be available, that is adapted to provide at least the controlling mode. Would other modes be available, the choice of such modes may especially be executed via a user interface, though other options, like executing a mode in dependence of a sensor signal or a (time) scheme, may also be possible. The operation mode may in embodiments also refer to a system, or apparatus, or device, that can only operate in a single operation mode (i.e. "on", without further tunability).

Hence, in embodiments, the control system may control in dependence of one or more of an input signal of a user interface, a sensor signal (of a sensor), and a timer. The term "timer" may refer to a clock and/or a predetermined time scheme.

Especially, in embodiments the control system may be configured to control the first light generating device and the second light generating device individually. This may e.g. allow a first device light only mode, or a first device light rich mode, and a second device light only more or a second device light rich mode.

In specific embodiments, the light generating system may further comprise a support, e.g. a PCB, though other supports may also be possible. Further, the light generating system may comprise a plurality n1 of first light generating devices and a plurality n2 of second light generating devices (both) configured to be supported by a support. The support may comprise a printed circuit board, though other options may also be possible.

In embodiments, $n2<n1$. In other embodiments $n2=n1$. Yet, in other embodiments $n2>n1$. Especially, in embodiments one or more of the following may apply, (i) $n1 \geq 2$ and (ii) $n2 \geq 2$. In specific embodiments, the first light generating devices may be configured in one or more rows.

In specific embodiments, the plurality n1 of first light generating devices and the plurality n2 of second light generating devices may comprise a subset comprising at least two first light generating devices and more than two second light generating devices, wherein especially all second light generating devices in the subset have equal second pitches p2. In this way, switching on or off or increasing or reducing intensity of the first light generating devices may have less or no impact on the homogeneous spatial distribution of the second device light.

In specific embodiments, $0.05 \leq n1/n2 \leq 0.75$. However, in other embodiments, $n1/n2 > 0.75$. Other values, however, like $n1/n2 < 0.05$ may also be possible.

In embodiments, the system may have an operational mode wherein essentially continuous white system is provided, including a (small) disinfection component provided by the first device light. In such embodiments, e.g. $n2>n1$.

In embodiments, the system may have a boost function, e.g. to disinfect at night or after using a room, etc. In such embodiments, $n2=n1$ or even $n2<n1$.

In embodiments, $n2=n1$ with e.g. a current splitter allowing a variable relative intensity of the first device light and second device light, including optionally only one of the first device light and second device light.

Optionally, downstream of the first light generating devices and/or second light generating devices, optics may be configured, such as beam shaping optics. The term "optics" may especially refer to (one or more) optical elements. Hence, the terms "optics" and "optical elements" may refer to the same items. The optics may include one or more or mirrors, reflectors, collimators, lenses, prisms, diffusers, phase plates, polarizers, diffractive elements, gratings, dichroics, arrays of one or more of the afore-mentioned, etc. Alternatively or additionally, the term "optics" may refer to a holographic element or a mixing rod. In embodiments, the optics may include one or more of beam expander optics and zoom lens optics. In embodiments, the optics may comprise light mixing optics. In embodiments, the light mixing optics may comprise one or more of diffusers (surface or volume scattering diffusers or engineered holographic optical elements), light pipes, light guides, Koehler integrator optics, etc. Alternatively or additionally, the light mixing optics may comprise a collimator or other collimating optics.

The terms "upstream" and "downstream" relate to an arrangement of items or features relative to the propagation of the light from a light generating means (here especially the light source), wherein relative to a first position within a beam of light from the light generating means, a second position in the beam of light closer to the light generating means is "upstream", and a third position within the beam of light further away from the light generating means is "downstream".

The light generating system may be part of or may be applied in e.g. office lighting systems, household application systems, shop lighting systems, home lighting systems, accent lighting systems, spot lighting systems, theater lighting systems, fiber-optics application systems, projection systems, self-lit display systems, pixelated display systems, segmented display systems, warning sign systems, medical lighting application systems, indicator sign systems, decorative lighting systems, portable systems, automotive applications, (outdoor) road lighting systems, urban lighting systems, green house lighting systems, horticulture lighting, digital projection, or LCD backlighting. The light generating system (or luminaire) may be part of or may be applied in e.g. optical communication systems or disinfection systems.

In yet a further aspect, the invention also provides a lamp or a luminaire comprising the light generating system as defined herein. The luminaire may further comprise a housing, optical elements, louvres, etc. etc . . . The lamp or luminaire may further comprise a housing enclosing the light generating system. The lamp or luminaire may comprise a light window in the housing or a housing opening, through which the system light may escape from the housing. In yet a further aspect, the invention also provides a projection device comprising the light generating system as defined herein. Especially, a projection device or "projector" or "image projector" may be an optical device that projects an image (or moving images) onto a surface, such as e.g. a projection screen. The projection device may include one or more light generating systems such as described herein. Hence, in an aspect the invention also provides a lighting device selected from the group of a lamp, a luminaire, a projector device, a disinfection device, a photochemical reactor, and an optical wireless communication device, comprising the light generating system as defined herein. The lighting device may comprise a housing or a carrier, configured to house or support, one or more elements of the light generating system. For instance, in embodiments the lighting device may comprise a housing or a carrier, configured to house or support one or more of the first light generating device, the second light generating device, the support, etc. Hence, the invention also provides lighting device selected from the group of a lamp, a luminaire, a disinfection device, and an optical wireless communication device, comprising the light generating system according as defined herein.

The invention also provides in an aspect a light generating system configured to generate system light, wherein: the first light generating device comprises a first light source and a first luminescent converter; and the first light source comprises a solid state light source, wherein the first light source is configured to generate first light source light having a first light source peak wavelength selected from the (about) range of 380-430 nm, more especially 380-420 nm. The invention also provides in an aspect a light generating system configured to generate system light, wherein: the first light generating device comprises a first light source and a first luminescent converter; and the first luminescent converter is configured to convert at least part of the first light source light into first converter light having a color point in the green-yellow wavelength range. Especially, the invention also provides in an aspect a light generating system configured to generate system light, wherein the light generating system comprises a first light generating device, wherein: (A) the first light generating device comprises a first light source and a first luminescent converter; (B) the first light source comprises a solid state light source, wherein the first light source is configured to generate first light source light having a first light source peak wavelength selected from the (about) range of 380-430 nm, more especially 380-420 nm; (C) the first luminescent converter is configured to convert at least part of the first light source light into first converter light having a color point in the green-yellow wavelength range; (D) the first light generating device is configured to generate first device light having a spectral power distribution in the wavelength range of 380-780 nm with at least 60% of the spectral power provided by the first light source light and at maximum 40% of the spectral power provided by the first converter light.

In yet a further aspect, the invention provides such first light generating device in combination with a second light generating device, wherein: (A) the second light generating device comprises a second light source and a second luminescent converter; (B) the second light source comprises a solid state light source, wherein the second light source is configured to generate second light source light (having a second light source peak wavelength selected from (about) the range of 440-490 nm); (C) the second luminescent converter is configured to convert at least part of the second light source light into second converter light (having a color point in the green-red wavelength range); (D) the second light generating device is configured to generate second device light having a spectral power distribution in the wavelength range of 380-780 nm with at least 60% of the spectral power provided by the second converter light and at maximum 40% of the spectral power provided by the second light source light, wherein the second device light is white light; (E) a first device light spectral power distribution of the first device light and a second device light spectral power distribution of the second device light may differ.

In yet a further aspect, the invention provides a method for treating at least part of a space or of an object (external of the light generating system or the light generating device), wherein the method may especially comprise providing system radiation comprising the first device light in the space or to the object, using the light generating system as defined herein or the lighting device as defined herein.

BRIEF DESCRIPTION OF THE DRAWINGS

Embodiments of the invention will now be described, by way of example only, with reference to the accompanying schematic drawings in which corresponding reference symbols indicate corresponding parts, and in which.

The schematic drawings are not necessarily to scale.

DETAILED DESCRIPTION OF THE EMBODIMENTS

Figure 1A:
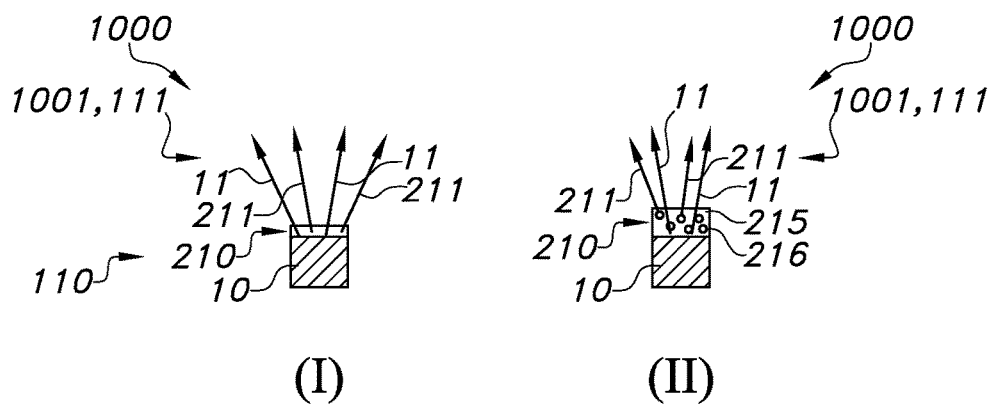
FIGS. 1a-1e schematically depict some aspects and embodiments.
Figure 1B:
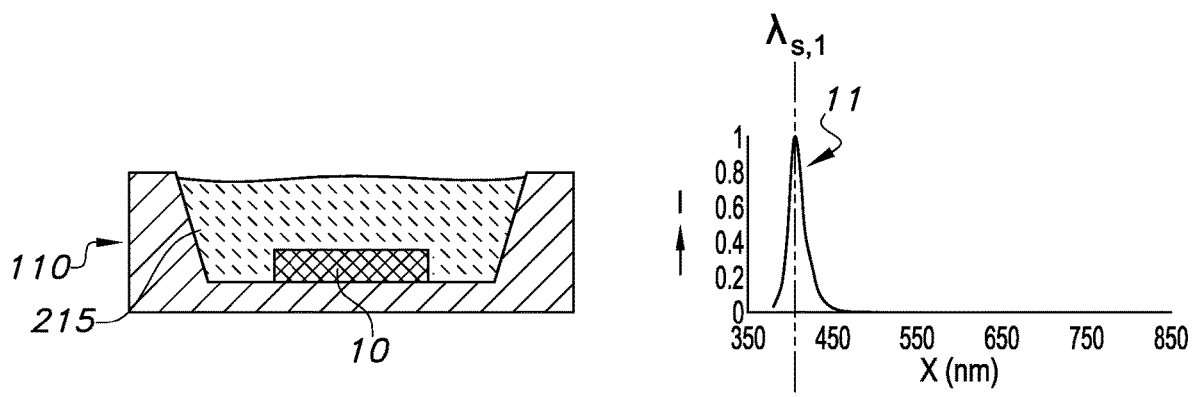
Figure 1B:
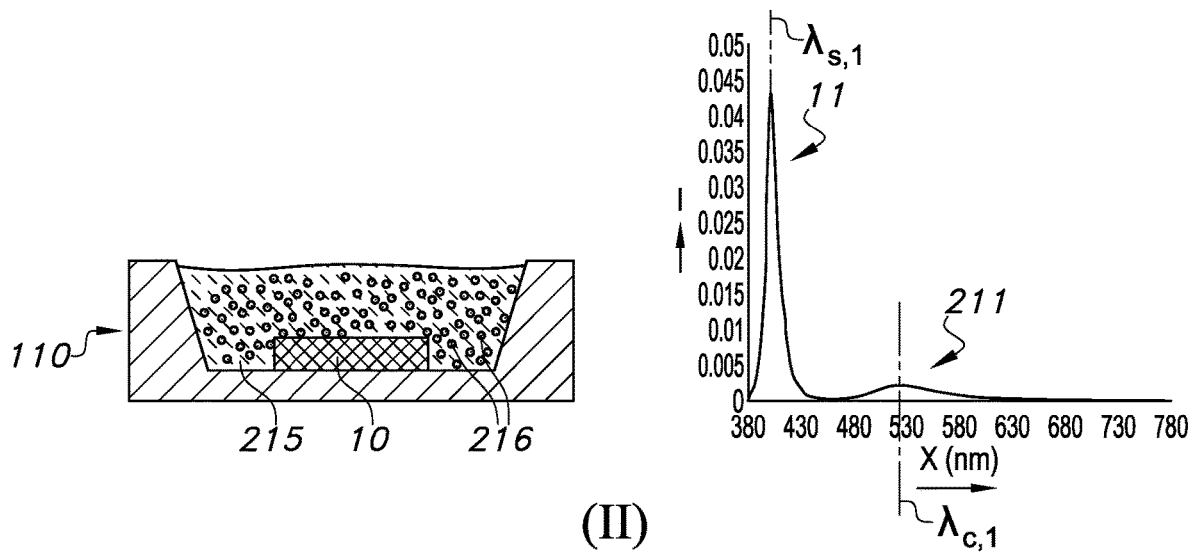

FIGS. 1a-1b schematically depict some embodiments and aspects. FIGS. 1a, embodiments I and II, and FIG. 1b, embodiments II, schematically depicts embodiments of a light generating system 1000 configured to generate system light 1001. The light generating system 1000 especially comprises a first light generating device 110. The first light generating device 110 may comprise a first light source 10 and a first luminescent converter 210. Especially, the first light source 10 may comprise a solid state light source. The first light source 10 may be configured to generate first light source light 11 having a first light source centroid wavelength $\lambda_{s,1}$, e.g. selected from the range of 380-430 nm, such as 380-425 nm, more especially 380-420 nm. The first luminescent converter 210 may be configured to convert (at least) part of the first light source light 11 into first converter light 211 having a first converter centroid wavelength $\lambda_{c,1}$, e.g. selected from the green-yellow wavelength range. Further, the first light generating device 110 may be configured to generate first device light 111 having a spectral power distribution in the wavelength range of 380-780 nm with e.g. at least 60% of the spectral power provided by the first light source light 11 and at maximum 40% of the spectral power provided by the first converter light 211.

In embodiments, the first light source centroid wavelength $\lambda_{s,1}$ may be selected from the range of 395-415 nm.

In embodiments, the first luminescent converter 210 may comprise a first matrix material 215 and a first luminescent material 216, wherein the first luminescent material 216 has a first weight percentage CW1 relative to the total weight of the first luminescent converter 210. In embodiments, CW1≤10 wt %.

Especially, the first luminescent converter 210 may be configured to convert the first light source light 11 into first converter light 211 having the first converter centroid wavelength $\lambda_{c,1}$ selected from the green wavelength range. However, other options may also be possible.

In embodiments, the first device light 111 may have a correlated color temperature selected from the range of 6000-25000 K. Further, the first device light 111 may have a (first device light) color point selected within 0-20 SDCM from the black body locus. Yet further, the first device light 111 may have and a color rendering index of at maximum 70. In embodiments, the first light source centroid wavelength $\lambda_{s,1}$ is selected from the range of 400-410 nm.

For an energy efficient and cost-efficient solution, a high efficiency is requested for both the first light generating device and second light generating device (like a white LED package). A device comprising a light source of blue+white LEDs may results in an overall efficacy reduction of around 22% below the standard white LED based device. This may be undesirable.

Some devices may have a relatively low probability of outcoupling from the clear silicone layer on top of the chip, e.g. as the surface is usually concave, at best nearly flat. An example of a first light generating device 110, but yet without first luminescent material, but with resin, here indicated with reference 215, is schematically depicted in FIG. 1b, embodiment I, on the left. An emission spectrum thereof is shown on the right of embodiment I. Essentially, the first device light of such device without first luminescent material, may consist of the first light source light 11.

Adding a violet light generating device may also shift the color point towards the blue (lower v'). In combination with standard white light generating devices this may limit the amount of violet light that can be added. A too high contribution of violet may shift the color point out of the ANSI-bin.

Amongst others, the invention proposes to add a minimum volume of phosphor particles in a short wavelength, especially about 405 nm, LED package, to provide a first light generating device, to promote light outcoupling and so improve efficiency, and induce some phosphor conversion to achieve a favorable color point. Especially, the combination of the violet pump light and the phosphor converted light can have a color point close to the BBL, allowing the addition of higher amounts of violet light in combination with standard white light generating devices, such as LEDs.

Using a violet light generating devices (without scatterer or phosphor) may result in a lower package efficiency as some of light is trapped inside the clear silicone (protection) layer on top of the chip. A portion of the light emitted by the chip will undergo total internal reflection at the air-silicone interface and will eventually get absorbed inside the package (by e.g. the die). Adding phosphor particles in the clear silicone may increase the light outcoupling due to more scattering inside the clear silicone layer, resulting in a larger probability of outcoupling.

FIG. 1b schematically shows the principle. The slightly changed spectrum is for this application beneficial (whitish color point). In a combination with standard white light generating devices, this may result in a white (within ANSI) color point. In a pure disinfection mode (switching on the 405 nm LED only), the emission will be cool white with a low color rendering. This mode may e.g. only used when no people are present in the room, therefore the low color rendering properties are acceptable (applying this concept with standard blue, green or red light generating devices would not be acceptable as it impacts the purity of the direct colors).

Hence, amongst others a bit of green/yellow phosphor may be provided in the 405 nm chip package, to provide a first light generating device, such that the color point of this package, i.e. the resulting first device light, shifts towards the BBL. At the same time, the extraction efficiency may thereby increase.

Figure 1C:
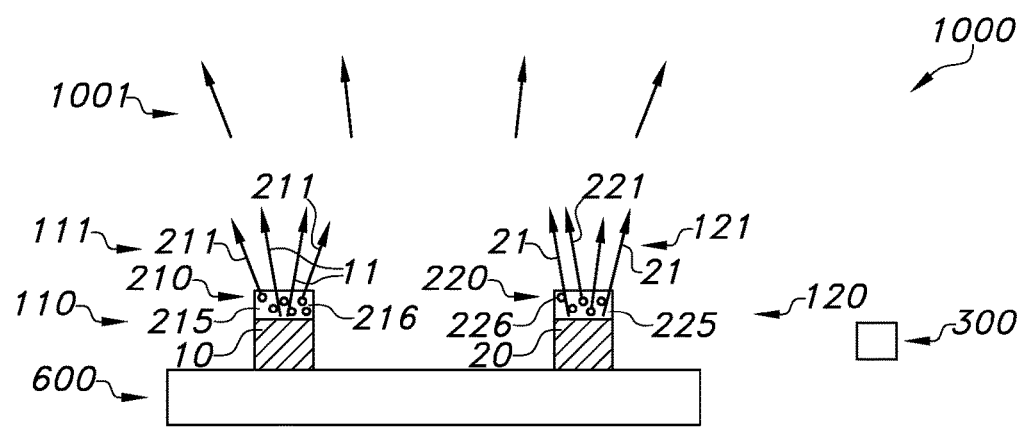
Figure 1D:
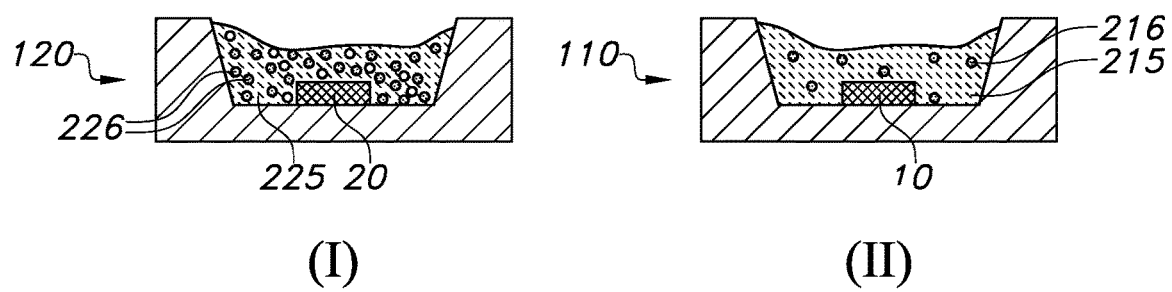
Figure 1E:
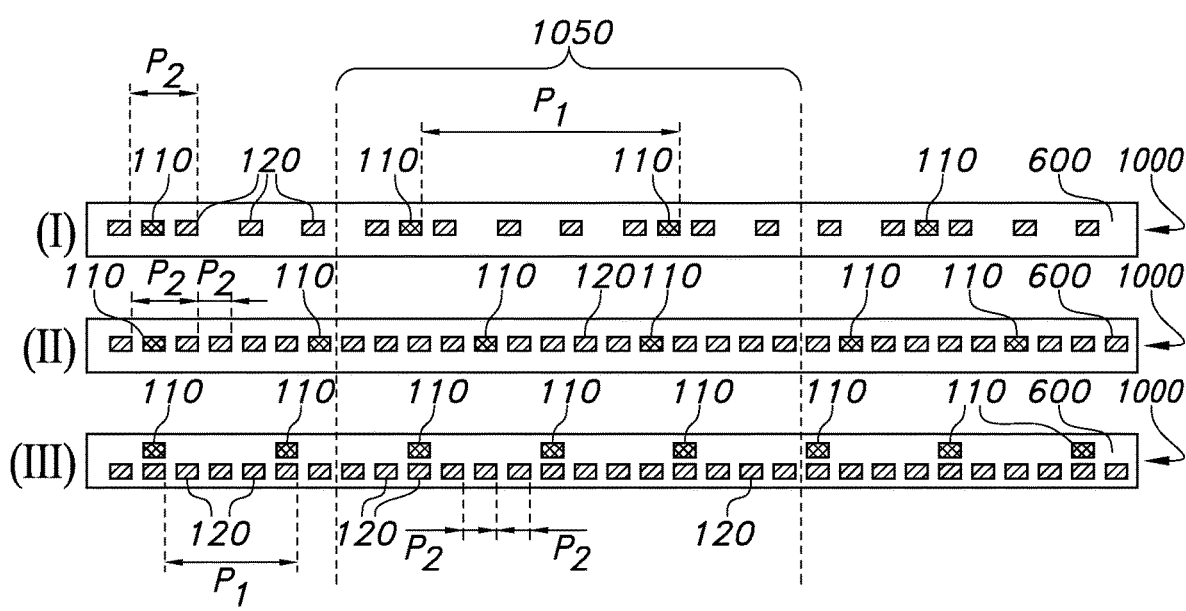

Referring to FIGS. 1c-1e, in specific embodiments the light generating system 1000 may further comprising a second light generating device 120. The second light generating device 120 may comprise a second light source 20 and a second luminescent converter 220. The second light source 20 may comprise a solid state light source. The second light source 20 may be configured to generate second light source light 21 (such as having a second light source centroid wavelength ($\lambda_{s,2}$) selected from the range of 440-490 nm). The second luminescent converter 220 may be configured to convert at least part of the second light source light 21 into second converter light 221 (such as having a second converter centroid wavelength ($\lambda_{c,2}$) selected from the green-red wavelength range). The second light generating device 120 may be configured to generate second device light 121 having a spectral power distribution in the wavelength range of 380-780 nm with at least 60% of the spectral power provided by the second converter light 221 and at maximum 40% of the spectral power provided by the second light source light 21. The second device light 121 may be white light. A first device light spectral power distribution of the first device light 111 and a second device light spectral power distribution of the second device light 121 may differ (see also below).

In embodiments, the second light source centroid wavelength ($\lambda_{s,2}$) may be selected from the range of 445-480 nm. The second luminescent converter 220 may comprise a second matrix material 225 and a second luminescent material 226. The second luminescent material 226 may have a second weight percentage CW2 relative to the total weight of the second luminescent converter 210. In embodiments, CW2 may be at least 20 wt %.

The second device light 121 may have a correlated color temperature selected from the range of 1800-6500 K, and a (second device light) color point within 0-15 SDCM from the black body locus, and a color rendering index of at minimum 70.

The first luminescent material 216 may comprise particulate material. The first matrix material 215 may comprise a resin (especially a silicone resin). The second luminescent material 226 may comprise particulate material. The second matrix material 225 may comprise a resin (especially a silicone resin). In embodiments, the first luminescent material 216 may comprise one or more of a $Eu^{2+}$-based luminescent material and a $Ce^{3+}$-based luminescent material.

In embodiments, CW1/CW2≤0.3. In embodiments, the first luminescent material 216 may have a first volume percentage CV1 of first luminescent material 216 in the first luminescent converter 210. Further, the second luminescent material 226 may have a second volume percentage V2 of the second luminescent material 226 in the second luminescent converter 220. In embodiments, CV1/V2≤0.3.

In embodiments, at least 50 wt % of the first luminescent material 216 has a particle dimension selected from the range of 1-20 µm.

In embodiments, relative to a spectral power distribution of the first converter light 211 in the range of 380-780 nm, at maximum 20% of the spectral power may be within the range of 585-780 nm.

In embodiments, relative to a spectral power distribution of the second device light 121 in the range of 380-780 nm, at maximum 30% of the spectral power may be provided by the second light source light 21.

In specific embodiments, the system light 1001 may have a correlated color temperature selected from the range of 1800-6500 K, and a (system light) color point within 0-10 SDCM from the black body locus, and a color rendering index of at minimum 70.

In embodiments, the light generating system 1000 may further comprising a control system 300. Especially, the control system 300 may be configured to control the system light 1001 in dependence of one or more of an input signal of a user interface, a sensor signal (of a sensor), and a timer. In embodiments, the control system 300 may be configured to control the first light generating device 110 and the second light generating device 120 individually.

Referring to FIG. 1e, the light generating system 1000 may further comprise a support 600. The light generating system 1000 may comprise a plurality n1 of first light generating devices 110 and a plurality n2 of second light generating devices 120 (both) configured supported by a support 600. In embodiments, the first light generating devices 110 are configured in one or more rows. In embodiments, the plurality n1 of first light generating devices 110 and the plurality n2 of second light generating devices 120 may comprise a subset 1050 comprising at least two first light generating devices 110 and more than two second light generating devices 120. In specific embodiments, all second light generating devices 120 in the subset 1050 have equal second pitches p2. Reference P1 refers to the pitch of the first light generating devices 110.

In embodiments, options range from adding the LEDs in the same row (I, II) or adding them next to the row of white LEDs (III). Also, in option I and III the resulting white LED positioning may be kept identical to the original white LED L2. As a result, the white light uniformity may be substantially unchanged; there may be no spottiness due to the violet as will be the case in option II. Proper luminaire optical design may still result in acceptable luminaire solutions with option II.

Figure 2:
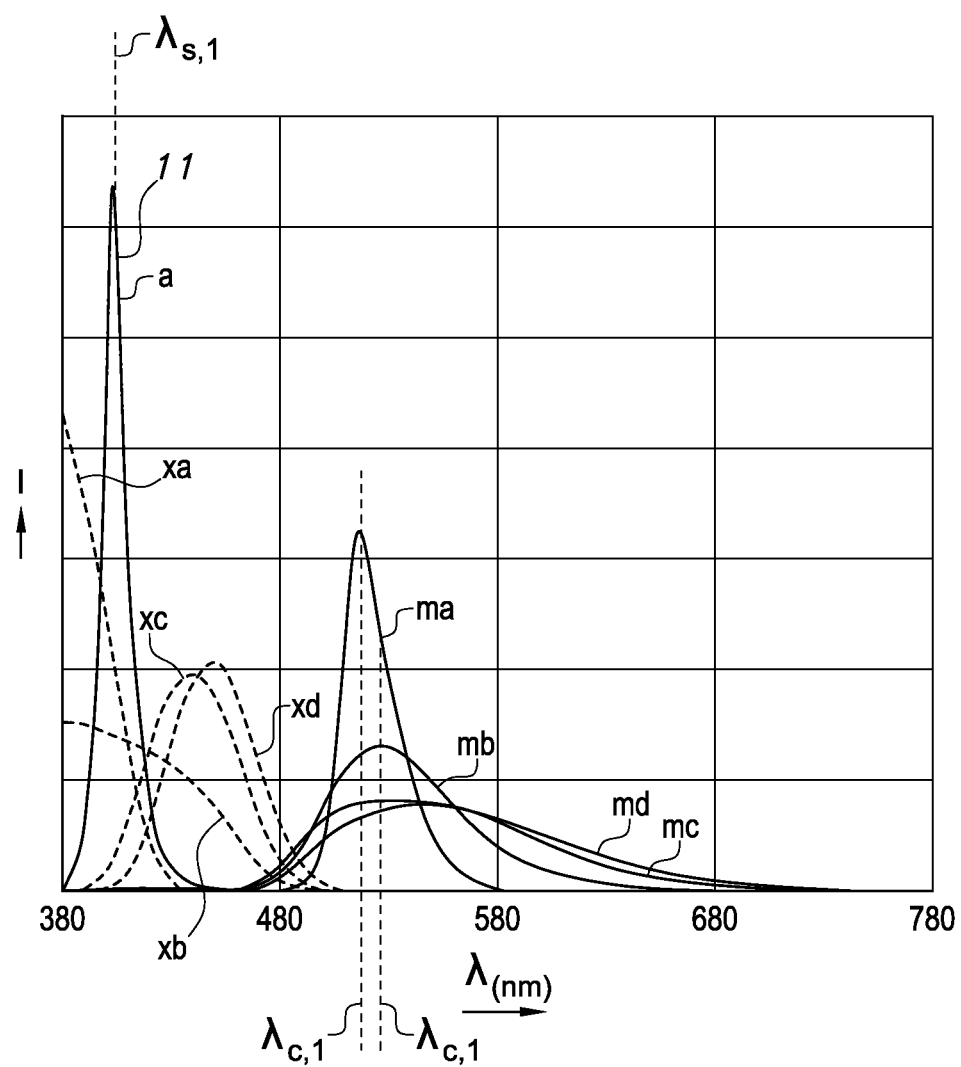
FIG. 2 shows some emission and excitation spectra.

FIG. 2 shows a short wavelength blue emission peak at about 405 nm peak wavelength/first light source centroid wavelength $\lambda_{s,1}$, as well as excitation spectra, indicated with the starting letter X and emission spectra indicated with the starting letter M of different luminescent materials. The luminescent materials are indicated with the second letters a, b, c, and d, and are: a divalent europium based narrow green phosphor (a), a divalent europium based silicate (b), a gallium comprising YAG-type luminescent material (c), and a lutetium comprising YAG-type material (d).

The excitation spectra (Xa and Xb) of the divalent europium based narrow green phosphor (a) and the divalent europium based silicate (b), respectively, have a good overlap with the first light source light 11; the excitation spectra (Xc and Xd) of the gallium comprising YAG-type luminescent material (c), and the lutetium comprising YAG-type material (d), respectively, have an overlap which is higher at the long wavelength side than at the short wavelength side of the first light source light 11.

By way of example centroid wavelengths $\lambda_{c,1}$ are schematically indicated for the emission ma of a divalent europium based narrow green phosphor (a), and for the emission mb of the divalent europium based silicate (b). Note that the schematically indicated centroid wavelengths herein may not necessarily exactly match with the calculated centroid wavelengths, as these centroid wavelengths are herein only indicated for reference purposes. Further, note that the centroid wavelengths do not necessarily coincide with peak wavelengths or maxima of emission bands.

Figure 3:
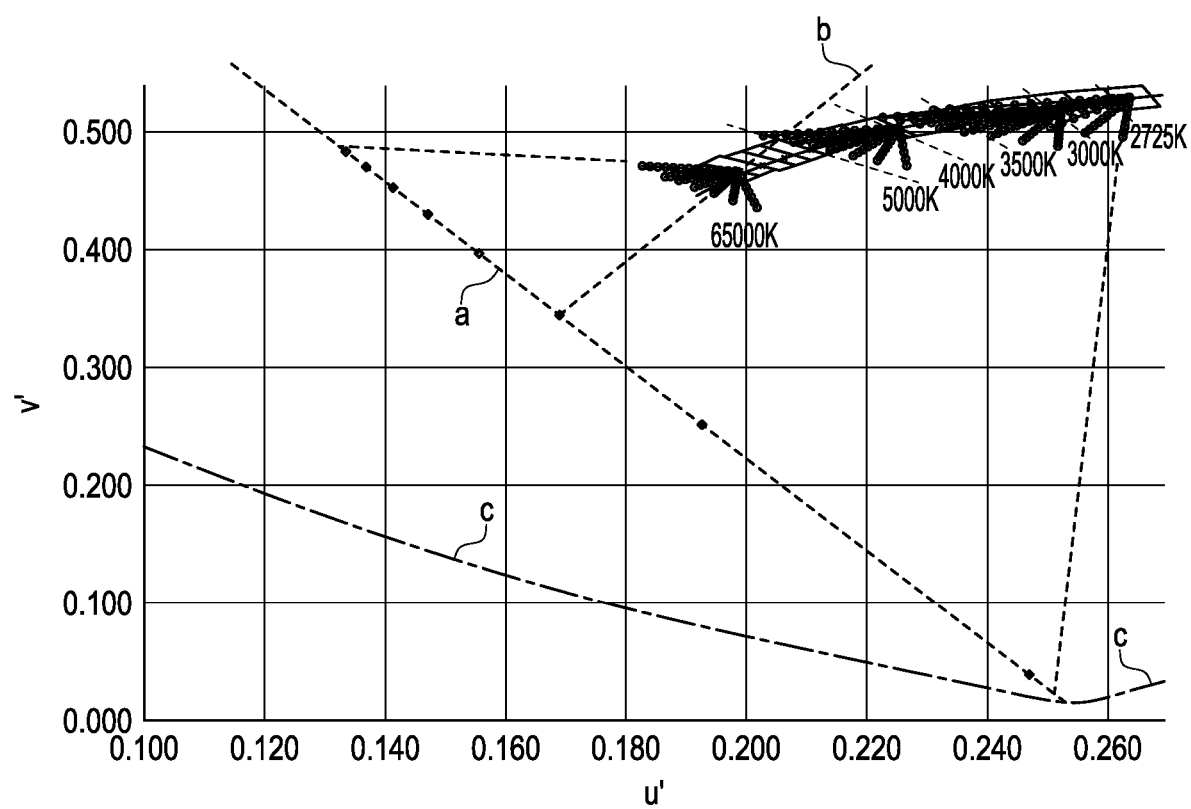
FIG. 3 shows a u'v' diagram with some light generating device (light) color points.

FIG. 3 depicts a u'v' color point plot of different light generating devices. By way of example, different standard white LEDs (2700 K, 3000 K, 4000 K and 6500 K) were combined with a violet LED. The white LEDs may e.g. have a high CRI, such as in embodiments CRI of ≥90. The violet LED may e.g. contain some divalent europium based phosphor, here especially in embodiments $BaSrSiO_4:Eu^{2+}$. The larger the amount of luminescent material, the higher the v' value.

Note that the color point of the first device light may thus be on a line connecting the color point of the second device light and color point of the desired application color point (and thus all three color points may be on the same line). The color point of first device light can be relatively far from BBL when the CCT of the second device light is relatively low. The color point of first device light can be relatively close to the BBL when the CCT of the second device light is relatively high. This is schematically shown using the 6500 K second device light example. A dashed dotted line b from a color point on or close to the BBL to a system light color point also on or close to the BBL would follow this dashed dotted line. The intersection with the line a, which shows the color point of the first device light as function of the relative amount (or volume) of first luminescent material (in a matrix), provides the color point of the first device light. Line c indicates part of the boundary of the color triangle.

The light of standard white LEDs is mixed with the light from violet pumped divalent europium based phosphor LEDs in different fractions, to generate color points at higher CCTs. Depending on the color point of the divalent europium based phosphor/405 nm LED the color point can go below BBL (too low divalent europium based phosphor thickness), along the BBL, or above BBL (too high divalent europium based phosphor thickness).

For the 2700 K white LED, the required phosphor thickness can be determined to generate color points along the BBL. The CCT of the violet LED is ~13000 K, with a CRI of ~39 and an R9 of −218. In the (combined color) point with the highest CCT (~3500 K) approximately 19% of the lumen flux is generated by the violet/$BaSrSiO_4:Eu^{2+}$ LED; CRI of the combined white spectrum is still 91. The white spectrum contains 1.7 mW of violet light/Lm.

For the 4000K white LED, the required phosphor thickness can be determined to generate color points along the BBL. The CCT of the violet LED would be ~21600 K, with a CRI of ~39 and an R9 of −198. In the (combined color) point with the highest CCT (5000K) approximately 16% of the lumen flux is generated by the violet/divalent europium based phosphor LED; CRI of the white spectrum is still 89. The white spectrum may contain 1.9 mW of violet light/Lm.

As can be derived from FIG. 3, in specific embodiments the first device light 111 may have a color point with u' selected from the range of 0.10-0.22 and with v' selected from the range of 0.30-0.55.

Figure 4A:
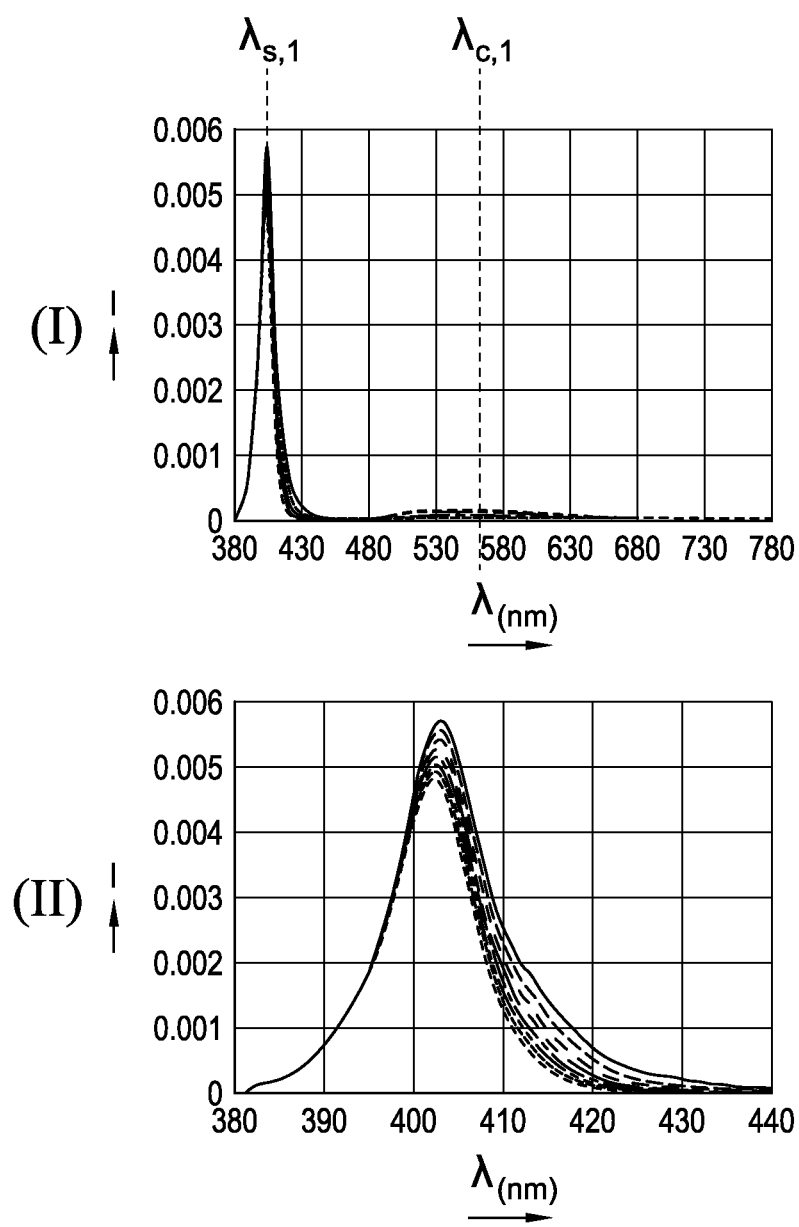
FIGS. 4a-4b show some LED spectra in dependence of the presence of a (first) luminescent material.
Figure 4B:
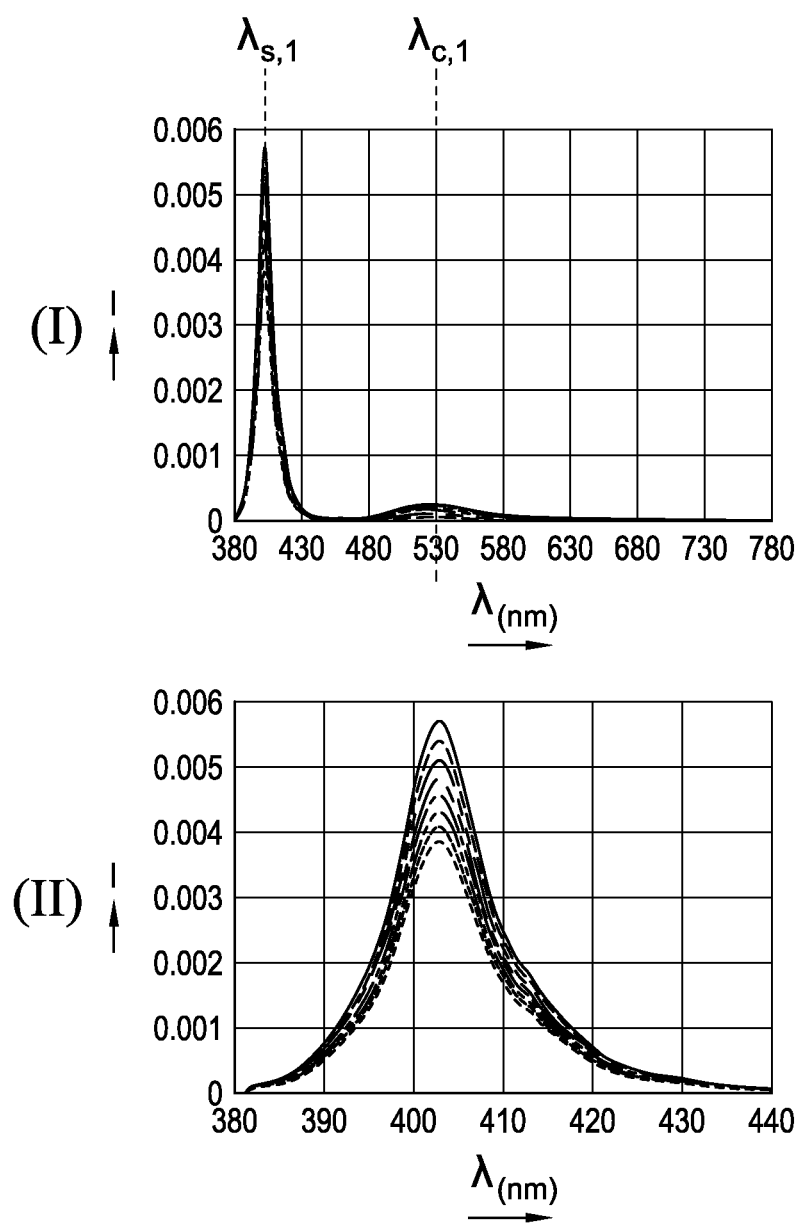

Cerium based green phosphors, such as in particular LuAG:Ce, may have a desirable excitation spectrum, see FIG. 4a. FIG. 4a shows in embodiment I the spectrum of the violet-based light generating device (first device light 111) as function of the amount of first luminescent material and in embodiment II the (remaining) emission of the first light source light 11 as function of the amount of first luminescent material. In FIG. 4b this is shown for a divalent europium based luminescent material. LuAG:Ce (FIG. 4a) absorbs mainly the long-wavelength part of the first light source light, which is expected to be slightly less effective in inactivating pathogens. So the more effective part of the spectrum remains.

The loss of 405 nm light by conversion can be compensated by increasing the relative amount of violet-based light generating devices, and the efficiency loss due to the larger Stokes shift for the phosphor converted light is very limited (~1%). The increase in PE due to the better outcoupling is more than expected to compensate for this effect.

Figure 5:
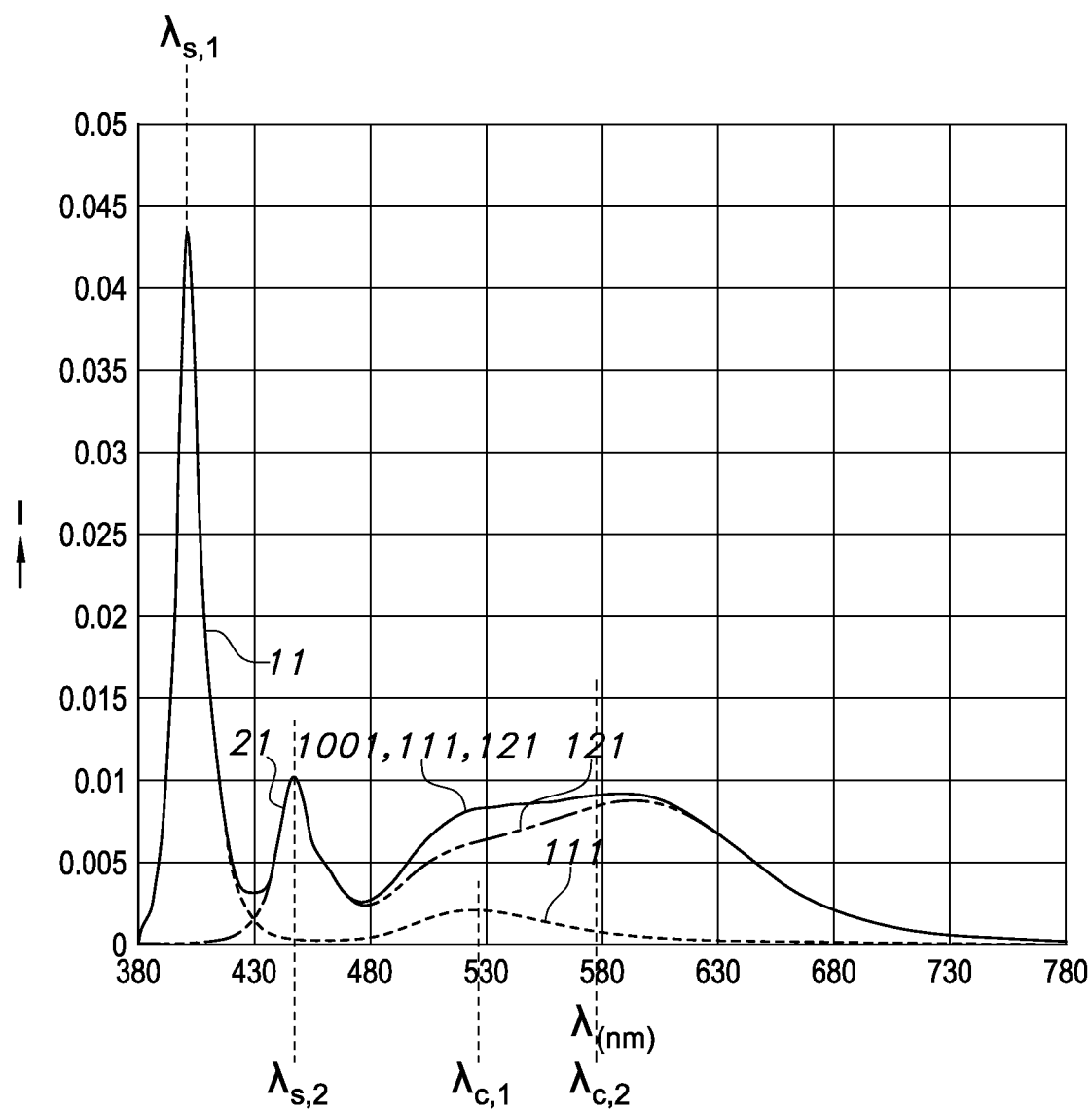
FIG. 5 shows an embodiment of system light.

FIG. 5 schematically depicts an embodiment of system light 1001, based on the composition with first device light 111 and second device light 121. Referring to the second device light 121, the spectral power distribution of the second device light 121 (in the wavelength range of 380-780 nm) may comprise in the range of 10-30% of the spectral power provided by the second light source light 21 and in the range of 70-90% of the spectral power provided by the second converter light.

Figure 6:
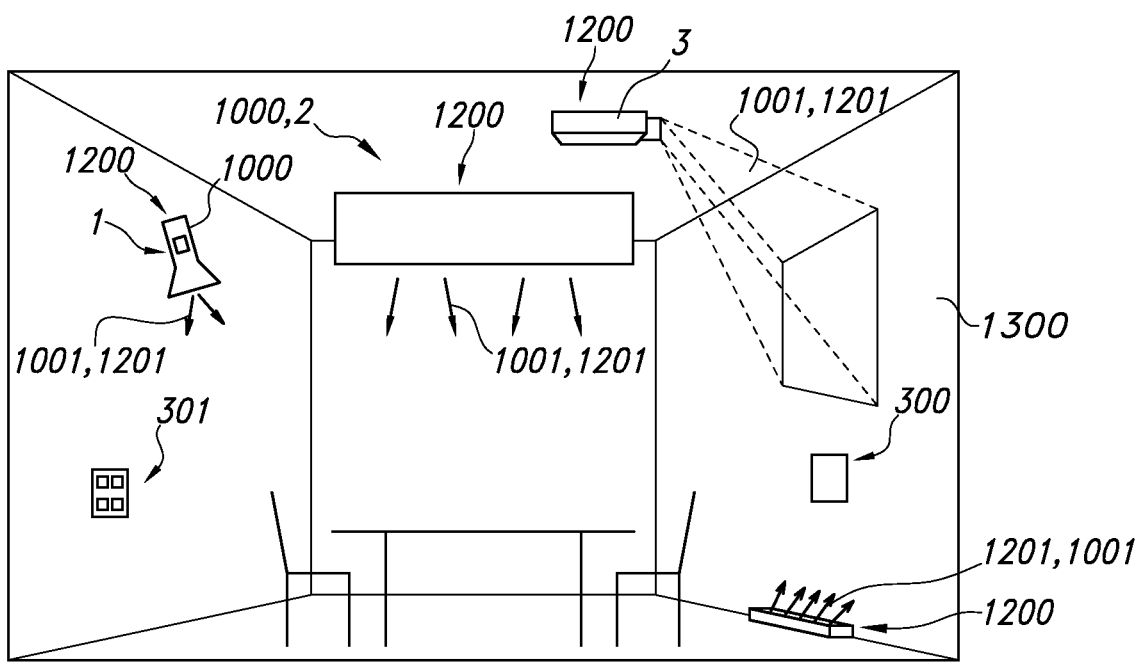
FIG. 6 schematically depicts some application embodiments.

FIG. 6 schematically depicts an embodiment of a luminaire 2 comprising the light generating system 1000 as described above. Reference 301 indicates a user interface which may be functionally coupled with the control system 300 comprised by or functionally coupled to the light generating system 1000. FIG. 6 also schematically depicts an embodiment of lamp 1 comprising the light generating system 1000. Reference 3 indicates a projector device or projector system, which may be used to project images, such as at a wall, which may also comprise the light generating system 1000. Hence, FIG. 6 schematically depicts embodiments of a lighting device 1200 selected from the group of a lamp 1, a luminaire 2, a projector device 3, a disinfection device, a photochemical reactor, and an optical wireless communication device, comprising the light generating system 1000 as described herein. In embodiments, such lighting device may be a lamp 1, a luminaire 2, a projector device 3, a disinfection device, or an optical wireless communication device. Lighting device light escaping from the lighting device 1200 is indicated with reference 1201. Lighting device light 1201 may essentially consist of system light 1001, and may in specific embodiments thus be system light 1001.

Amongst others, with the present invention a method for treating at least part of a space 1300 or of an object (external of the light generating system 1000 or the light generating device 1200) may be provided. The method may comprise providing system radiation 1001 comprising the first device light 111 in the space 1300 or to the object, using the light generating system 1000 as described herein or the lighting device 1200 as described herein.

The term "plurality" refers to two or more.

The terms "substantially" or "essentially" herein, and similar terms, will be understood by the person skilled in the art. The terms "substantially" or "essentially" may also include embodiments with "entirely", "completely", "all", etc. Hence, in embodiments the adjective substantially or essentially may also be removed. Where applicable, the term "substantially" or the term "essentially" may also relate to 90% or higher, such as 95% or higher, especially 99% or higher, even more especially 99.5% or higher, including 100%.

The term "comprise" also includes embodiments wherein the term "comprises" means "consists of".

The term "and/or" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices, apparatus, or systems may herein amongst others be described during operation. As will be clear to the person skilled in the art, the invention is not limited to methods of operation, or devices, apparatus, or systems in operation.

It should be noted that the above-mentioned embodiments illustrate rather than limit the invention, and that those skilled in the art will be able to design many alternative embodiments without departing from the scope of the appended claims.

In the claims, any reference signs placed between parentheses shall not be construed as limiting the claim.

Use of the verb "to comprise" and its conjugations does not exclude the presence of elements or steps other than those stated in a claim. Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

The article "a" or "an" preceding an element does not exclude the presence of a plurality of such elements.

The invention may be implemented by means of hardware comprising several distinct elements, and by means of a suitably programmed computer. In a device claim, or an apparatus claim, or a system claim, enumerating several means, several of these means may be embodied by one and the same item of hardware. The mere fact that certain measures are recited in mutually different dependent claims does not indicate that a combination of these measures cannot be used to advantage. In yet a further aspect, the invention (thus) provides a software product, which, when running on a computer is capable of bringing about (one or more embodiments of) the method as described herein.

The invention also provides a control system that may control the device, apparatus, or system, or that may execute the herein described method or process. Yet further, the invention also provides a computer program product, when running on a computer which is functionally coupled to or comprised by the device, apparatus, or system, controls one or more controllable elements of such device, apparatus, or system.

The invention further applies to a device, apparatus, or system comprising one or more of the characterizing features described in the description and/or shown in the attached drawings. The invention further pertains to a method or process comprising one or more of the characterizing features described in the description and/or shown in the attached drawings.

The various aspects discussed in this patent can be combined in order to provide additional advantages. Further, the person skilled in the art will understand that embodiments can be combined, and that also more than two embodiments can be combined. Furthermore, some of the features can form the basis for one or more divisional applications.

The invention claimed is:

1. A light generating system configured to generate system light, wherein the light generating system comprises a first light generating device; wherein:
   the first light generating device comprises a first light source and a first luminescent converter;
   the first light source comprises a solid state light source, wherein the first light source is configured to generate first light source light having a first light source centroid wavelength selected from the range of 380-420 nm;
   the first luminescent converter is configured to convert part of the first light source light into first converter light having a first converter centroid wavelength selected from the green-yellow wavelength range;
   the first light generating device is configured to generate first device light having a spectral power distribution in the wavelength range of 380-780 nm with at least 60% of the spectral power provided by the first light source light and at maximum 40% of the spectral power provided by the first converter light;
   wherein the first luminescent converter comprises a first matrix material and a first luminescent material, wherein the first luminescent material has a first weight percentage CW1 relative to the total weight of the first luminescent converter;
   wherein the light generating system further comprises a second light generating device, wherein the second light generating device comprises a second light source and a second luminescent converter; wherein the second light source comprises a solid state light source, wherein the second light source is configured to generate second light source light; wherein the second luminescent converter is configured to convert at least part of the second light source light into second converter light; and wherein the second light generating device is configured to generate second device light having a spectral power distribution in the wavelength range of 380-780 nm with at least 60% of the spectral power provided by the second converter light and at maximum 40% of the spectral power provided by the second light source light;
   wherein the second luminescent converter comprises a second matrix material and a second luminescent material, wherein the second luminescent material has a second weight percentage CW2 relative to the total weight of the second luminescent converter; and wherein CW1/CW2≤0.5.

2. The light generating system according to claim 1, wherein the first light source centroid wavelength is selected from the range of 395-415 nm, wherein the first luminescent converter is configured to convert the first light source light into first converter light having the first converter centroid wavelength selected from the green wavelength range.

3. The light generating system according to claim 1, wherein CW1≤10 wt %; wherein the first light source centroid wavelength is selected from the range of 400-410 nm; and wherein the first device light has a color point with u' selected from the range of 0.10-0.22 and with v' selected from the range of 0.30-0.55.

4. The light generating system according to claim 1, wherein the second device light is white light.

5. The light generating system according to claim 4, wherein the second light source light having a second light source centroid wavelength selected from the range of 445-480 nm; wherein the second device light has a correlated color temperature selected from the range of 1800-6500 K, and a color point within 0-15 SDCM from the black body locus, and a color rendering index of at minimum 70.

6. The light generating system according to claim 1, wherein CW1/CW2≤0.3; wherein the first luminescent material comprises particulate material, and wherein the first matrix material comprises a resin; wherein the second luminescent material comprises particulate material, and wherein the second matrix material comprises a resin.

7. The light generating system according to claim 1, wherein CW2 is at least 20 wt %.

8. The light generating system according to claim 1, wherein:
   at least 50 wt % of the first luminescent material has a particle dimension selected from the range of 1-20 μm;
   relative to a spectral power distribution of the first converter light in the range of 380-780 nm, at maximum 20% of the spectral power is within the range of 585-780 nm; and
   relative to a spectral power distribution of the second device light in the range of 380-780 nm, at maximum 30% of the spectral power is provided by the second light source light.

9. The light generating system according to claim 1, wherein the first luminescent material comprises one or more of a $Eu^{2+}$—based luminescent material and a $Ce^{3+}$—based luminescent material.

10. The light generating system according to claim 1, wherein the system light has a correlated color temperature selected from the range of 1800-6500 K, and a color point within 0-10 SDCM from the black body locus, and a color rendering index of at minimum 70.

11. The light generating system according to claim 1, further comprising a control system, wherein the control system is configured to control the system light in dependence of one or more of an input signal of a user interface, a sensor signal, and a timer.

12. The light generating system according to claim 11, wherein the control system is configured to control the first light generating device and the second light generating device individually.

13. The light generating system according to claim 1, further comprising a support, wherein:
   the light generating system comprises a plurality n1 of first light generating devices and a plurality n2 of second light generating devices configured supported by a support;
   the plurality n1 of first light generating devices and the plurality n2 of second light generating devices comprise a subset comprising at least two first generating devices and more than two second light generating devices, wherein all second light generating devices in the subset have equal second pitches.

14. A lighting device selected from the group of a lamp, a luminaire, a disinfection device, and an optical wireless communication device, comprising the light generating system according to claim 1.

15. A method for treating at least part of a space or of an object, wherein the method comprises providing system radiation comprising the first device light in the space or to the object, using the light generating system as defined in claim 1.

* * * * *